US007700650B2

(12) United States Patent
Van Dyke et al.

(10) Patent No.: US 7,700,650 B2
(45) Date of Patent: Apr. 20, 2010

(54) LIPOXIN ANALOGS AND METHOD FOR THE TREATMENT OF PERIODONTAL DISEASE

(75) Inventors: Thomas E. Van Dyke, West Roxbury, MA (US); Nicos A. Petasis, Hacienda Heights, CA (US); Charles N. Serhan, Needham, MA (US)

(73) Assignees: Trustees of Boston University, Boston, MA (US); Brigham and Women's Hospital, Inc., Boston, MA (US); University of Southern California, Los Angeles, CA (US)

( * ) Notice: Subject to any disclaimer, the term of this patent is extended or adjusted under 35 U.S.C. 154(b) by 742 days.

(21) Appl. No.: 10/239,444

(22) PCT Filed: Mar. 20, 2001

(86) PCT No.: PCT/US01/09096
§ 371 (c)(1),
(2), (4) Date: Sep. 20, 2002

(87) PCT Pub. No.: WO01/70664
PCT Pub. Date: Sep. 27, 2001

(65) Prior Publication Data
US 2004/0019110 A1    Jan. 29, 2004

Related U.S. Application Data

(60) Provisional application No. 60/190,656, filed on Mar. 20, 2000.

(51) Int. Cl.
*A01N 37/06* (2006.01)
(52) U.S. Cl. .................. 514/549; 514/560; 554/213
(58) Field of Classification Search ............. 554/224, 554/213; 514/552, 549, 560
See application file for complete search history.

(56) References Cited

U.S. PATENT DOCUMENTS 5,441,951 A * 8/1995 Serhan ................. 554/224

(Continued)

FOREIGN PATENT DOCUMENTS

WO    WO 94 29262    12/1994

(Continued)

OTHER PUBLICATIONS

Serhan et al., Adv. in Exp. Med. & Bio., "Aspirin-triggered 15-epi-lipoxin A4 and novel lipoxin in vascular permeability", pp. 287-293, 1999.*

(Continued)

*Primary Examiner*—Deborah D Carr
(74) *Attorney, Agent, or Firm*—Choate, Hall & Stewart LLP; Charles E. Lyon

(57) ABSTRACT

This invention provides new lipoxin analogs, compositions containing these analogs, and methods of using these compounds and compositions for treating and preventing oral inflammation, including gingivitis, periodontitis, and other forms of periodontal disease. The invention also provides for methods of treating and preventing oral inflammation, including gingivitis, periodontitis, and other forms of periodontal disease with compositions containing COX-2 inhibitors. Further, the invention provides methods for preventing systemic diseases beyond the oral cavity that are related to periodontal disease using the compositions containing lipoxin analogs, COX-2 inhibitors, or both.

29 Claims, 6 Drawing Sheets

U.S. PATENT DOCUMENTS

| | | | | |
|---|---|---|---|---|
| 5,648,512 | A | | 7/1997 | Serhan |
| 5,650,435 | A | * | 7/1997 | Madara et al. ............... 514/552 |
| 5,998,487 | A | | 12/1999 | Shapiro et al. |
| 6,048,897 | A | * | 4/2000 | Serhan ........................ 514/560 |
| 6,316,648 | B1 | | 11/2001 | Serhan ........................ 554/213 |
| 6,569,075 | B2 | * | 5/2003 | Serhan ........................ 554/213 |
| 6,620,919 | B2 | * | 9/2003 | Serhan ........................ 554/213 |
| 6,635,776 | B2 | * | 10/2003 | Serhan ........................ 554/213 |
| 6,653,493 | B2 | | 11/2003 | Serhan ........................ 554/218 |
| 6,670,396 | B2 | | 12/2003 | Serhan et al. ............... 514/549 |
| 6,750,360 | B2 | * | 6/2004 | Serhan ........................ 554/213 |
| 6,887,901 | B1 | * | 5/2005 | Serhan ........................ 514/560 |
| 2001/0023500 | A1 | | 9/2001 | Serhan |
| 2001/0031882 | A1 | | 10/2001 | Serhan |
| 2002/0010351 | A1 | | 1/2002 | Serhan |
| 2002/0045579 | A1 | | 4/2002 | Madara et al. |
| 2002/0055538 | A1 | | 5/2002 | Serhan et al. |
| 2002/0082435 | A1 | | 6/2002 | Serhan |
| 2002/0091279 | A1 | | 7/2002 | Serhan |
| 2002/0094549 | A1 | | 7/2002 | Serhan et al. |
| 2002/0107289 | A1 | | 8/2002 | Serhan |
| 2002/0111505 | A1 | | 8/2002 | Serhan |
| 2002/0120013 | A1 | | 8/2002 | Serhan |
| 2002/0132847 | A1 | | 9/2002 | Serhan |
| 2002/0143069 | A1 | | 10/2002 | Serhan |
| 2002/0193431 | A1 | | 12/2002 | Serhan et al. |
| 2003/0032827 | A1 | | 2/2003 | Serhan |
| 2003/0055275 | A1 | | 3/2003 | Serhan |
| 2003/0060512 | A1 | | 3/2003 | Madara et al. |
| 2003/0069435 | A1 | | 4/2003 | Serhan |
| 2003/0134901 | A1 | | 7/2003 | Serhan |
| 2003/0166716 | A1 | | 9/2003 | Serhan et al. |
| 2003/0191184 | A1 | | 10/2003 | Serhan et al. |
| 2003/0191332 | A1 | | 10/2003 | Serhan |
| 2003/0195248 | A1 | | 10/2003 | Serhan et al. |
| 2004/0019110 | A1 | | 1/2004 | Van Dyke et al. |
| 2004/0053998 | A1 | | 3/2004 | Serhan et al. |
| 2004/0059144 | A1 | | 3/2004 | Serhan et al. |
| 2004/0116408 | A1 | | 6/2004 | Serhan |
| 2004/0151712 | A1 | | 8/2004 | Madara et al. |
| 2004/0192785 | A1 | | 9/2004 | Serhan |
| 2005/0075398 | A1 | | 4/2005 | Bazan et al. |

FOREIGN PATENT DOCUMENTS

| | | |
|---|---|---|
| WO | WO 95 01179 | 1/1995 |
| WO | WO 98 11049 | 3/1998 |
| WO | WO 00 13685 | 3/2000 |
| WO | WO 01 41753 | 6/2001 |

OTHER PUBLICATIONS

Pouliot et al., Biochemistry, pp. 4761-4768, 2000.*

Pouliot et al., J Periodonttal Research, 1999; 34: 370-373.*

M. Poulot, C.N. Serhan, "Lipoxin A4 and Aspirin-Triggered 15-epi-LXA4 Inhibit Tumor Necrosis Factor-.alpha.-initiated Neutrophil Responses . . . ", *Journal of Periodontal Research*, vol. 34, No. 7 (1999), pp. 370-373.

K.C. Nicolaou et al., "Total Synthesis of Novel Geometric Isomers of Lipoxin A4 and Lipoxin B4", *Journal of Organic Chemistry*, vol. 54 (1989), pp. 5527-5535.

J. Nokami et al., Palladium-catalyzed Coupling Reactions of Bromobenzaldehydes with 3,4-Di(tert-butyldimethylsilyloxy-)1-alken e to (3,4-Dihydroxyalkenyl) benzaldehydes in the Synthesis of Lipoxin Analogoues, *Tetrahedron Letters*, vol. 39 (1998), pp. 1005-1008.

Serhan, "Design of Lipoxin A4 Stable Analogs . . . ", *Biochemistry*, vol. 34 (1995) pp. 14609-21415.

Maddox, "Lipoxin B4 Regulates Human . . . ", *The FASEB Journal*, vol. 12 (1998) pp. 487-494.

Anne-Marie Nguyen et al., "Nonsteroidal Anti-Inflammatory Drug Use in Dentistry: Gastrointestinal Implications", *General Dentistry*, vol. 47, No. 6, Nov. 1999, pp. 590-596.

Bandeira-Melo C, et al., "Cutting Edge: Lipoxin (LX) A4 and Aspirin-Triggered 15-epi-LXA4 Block Allergen-Induced Eosinophil Trafficking.", *J Immunol.* 164(5): 2267-71,2000.

Chiang N, et al., "Aspirin-Triggered 15-epi-Lipoxin A4 (ATL) Generation by Human Leukocytes and Murine Peritonitis Exudates: Development of a Specific 15-epi-LXA4 Elisa.", *J Pharmacol Exp Ther.* 287(2): 779-90, 1998.

Clish CB, et al., "Local and Systemic Delivery of a Stable Aspirin-Triggered Lipoxin Prevents Neutrophil Recruitment In Vivo.", *Proc Natl Acad Sci U S A.* 96(14): 8247-52, 1999.

Filep JG, et al., "Anti-Inflammatory Actions of Lipoxin A(4) Stable Analogs Are Demonstrable in Human Whole Blood: Modulation of Leukocyte Adhesion Molecules and Inhibition of Neutrophil-Endothelial Interactions.", *Blood.* 94(12): 4132-42, 1999.

Gerwitz AT, et al., "LXA4, Aspirin-Triggered 15-epi-LXA4, and Their Analogs Selectively Downregulate PMN Azurophilic Degranulation.", *Am J Physiol.* 276(4 Pt 1): C988-94, 1999.

Gronert K, et al., "Identificatin of a Human Enterocyte Lipoxin A4 Receptor That is Regulated by Interleukin (IL)-13 and Interferon Gamma and Inhibits Tumor Necrosis Factor Alpha-Induced IL-8 Release.", *J Exp Med.* 187(8): 1285-94, 1998.

Hachicha M, et al., "Lipoxin (LX)A4 and Aspirin-Triggered 15-epi-LXA4 Inhibit Tumor Necrosis Factor 1 Alpha-Initiated Neutrophil Responses and Trafficking: Regulators of a Cytokine-Chemokine Axis.", *J Exp Med* 189(12): 1923-30, 1999.

Maddox JF, et al., "Lipoxin A4 Stable Analogs Are Potent Mimetics That Stimulate Human Monocytes and THP-1 Cells Via a G-Protein-Linked Lipoxin A4 Receptor.", *J Biol Chem.* 272(11): 6972-8, 1997.

Maddox JF, et al., "Lipoxin B4 Regulates Human Monocyte/ Neutrophil Adherence and Motility: Design of Stable Lipoxin B4 Analogs With Increased Biologic Activity.", *FASEB J.* 12(6): 487-94, 1998.

Serhan CN, et al., "Aspirin-Triggered 15-epi-Lipoxin A4 and Stable Analogs on Lipoxin A4 Are Potent Inhibitors of Acute Inflammation.", *Adv Exp Med Biol.* 447: 133-49, 1999.

Serhan CN, et al., "Lipoxin and Aspirin-Triggered I5-epi-Lipoxin Cellular Interactions Anti-Inflammatory Lipid Mediators.", *Clin Chem Lab Med.* 37(3): 299-309, 1999.

Serhan CN, et al., "Lipoxins, Aspirin-Triggered 15-epi-Lipoxin Stable Analogs and Their Receptors in Anti-Inflammation: A Window for Therapeutic Opportunity.", *Ernst Schering Re Found Workshop* 31: 143-85, 2000.

Serhan CN, "Lipoxins and Novel Aspirin-Triggered 15-epi-Lipoxins (ATL): A Jungle of Cell-Cell Interactions or a Therapeutic Opportunity?", *Prostaglandins.* 53(2): 107-37, 1997.

Takano T, et al., "Aspirin-Triggered 15-epi-Lipoxin A4 (LXA4) and LXA4 Stable Analogues Are Potent Inhibitors of Acute Inflammation: Evidence for Anti-Inflammatory Receptors.", *J Exp Med.* 185(9): 1693-704, 1997.

Takano T, et al., "Neutrophil-Mediated Changes in Vascular Permeability Are Inhibited by Topical Application of Aspirin-Triggered 15-epi-Lipoxin A4 and Novel Lipoxin B4 Stable Analogues.", *J Clin Invest.* 101(4): 819-26, 1998.

Titos E, et al., "Hepatocytes Are a Rich Source of Novel Aspirin-Triggered 15-epi-Lipoxin A(4)", *Am J Physiol.* 277(5 Pt 1): C870-7, 1999.

* cited by examiner

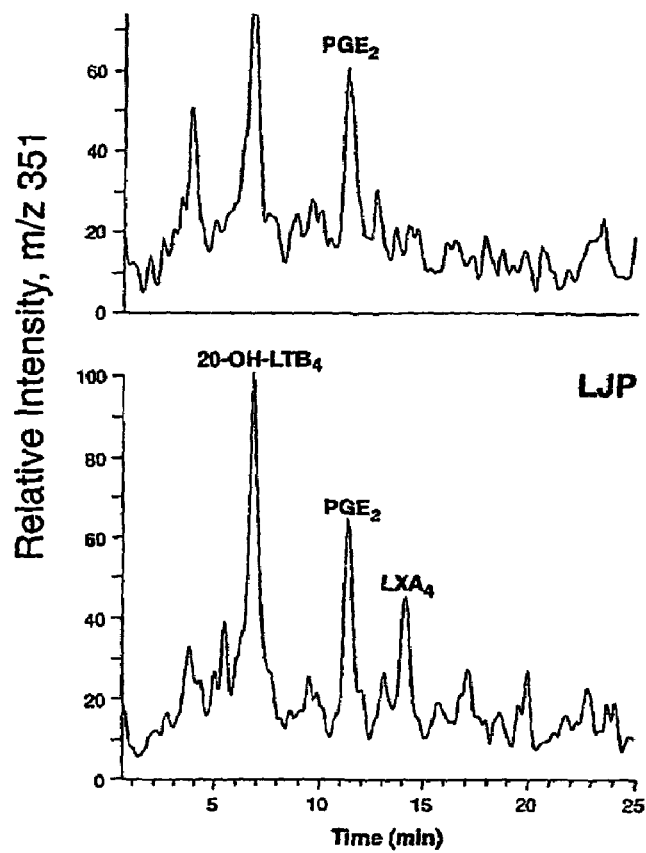

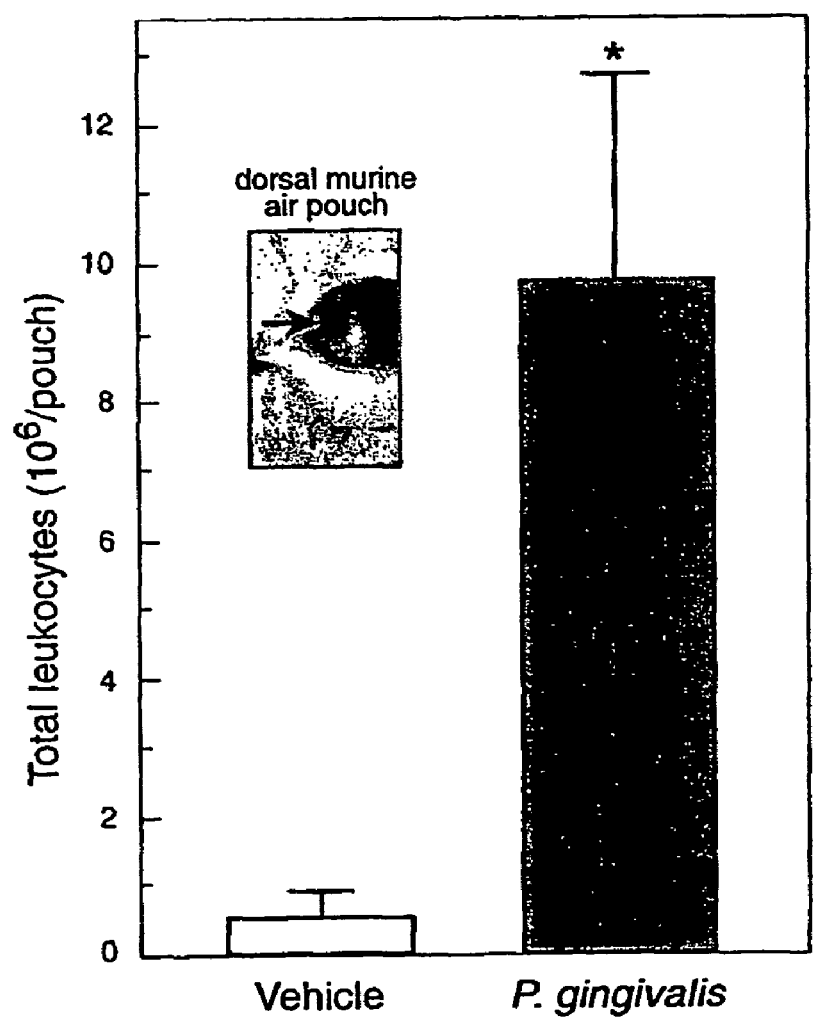
Fig_2

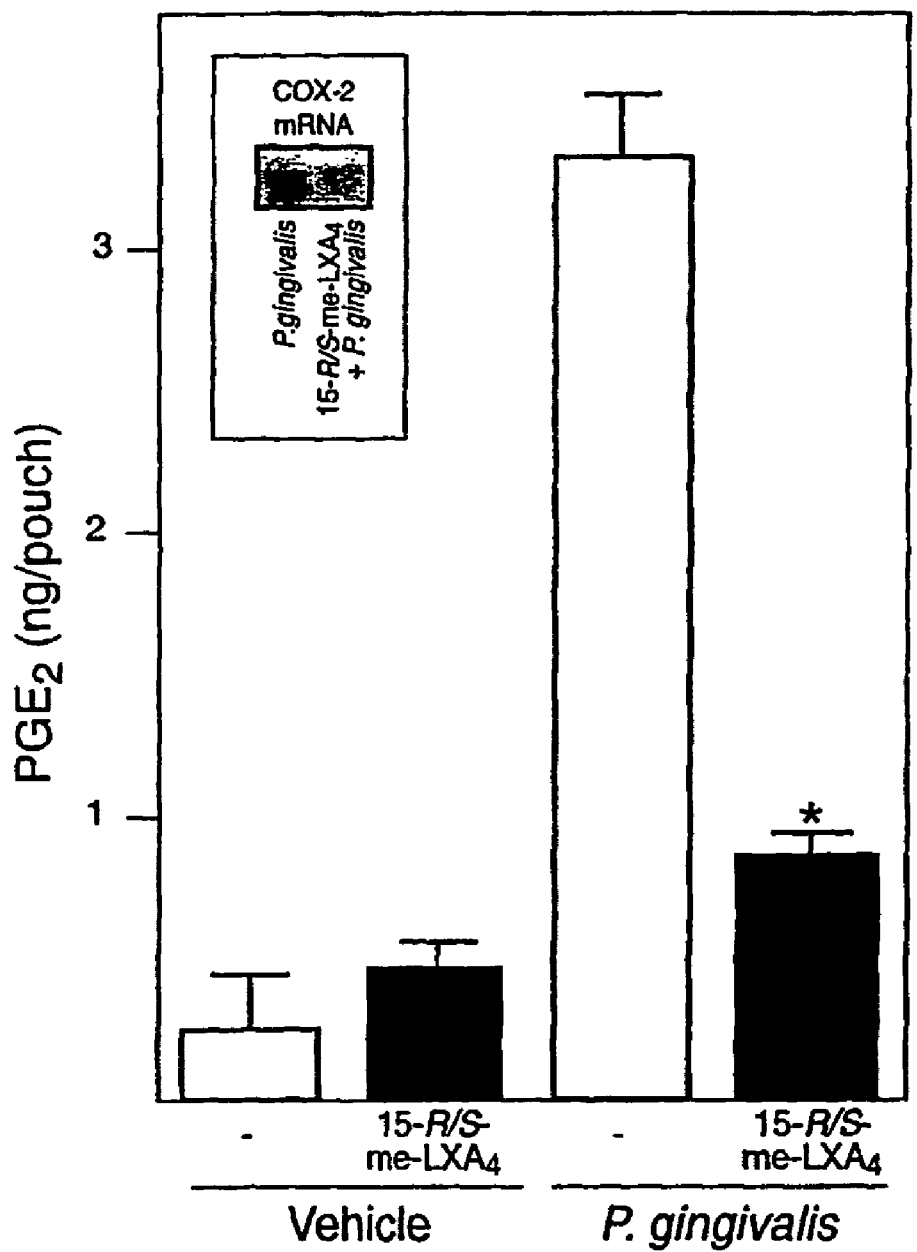
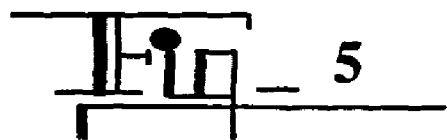

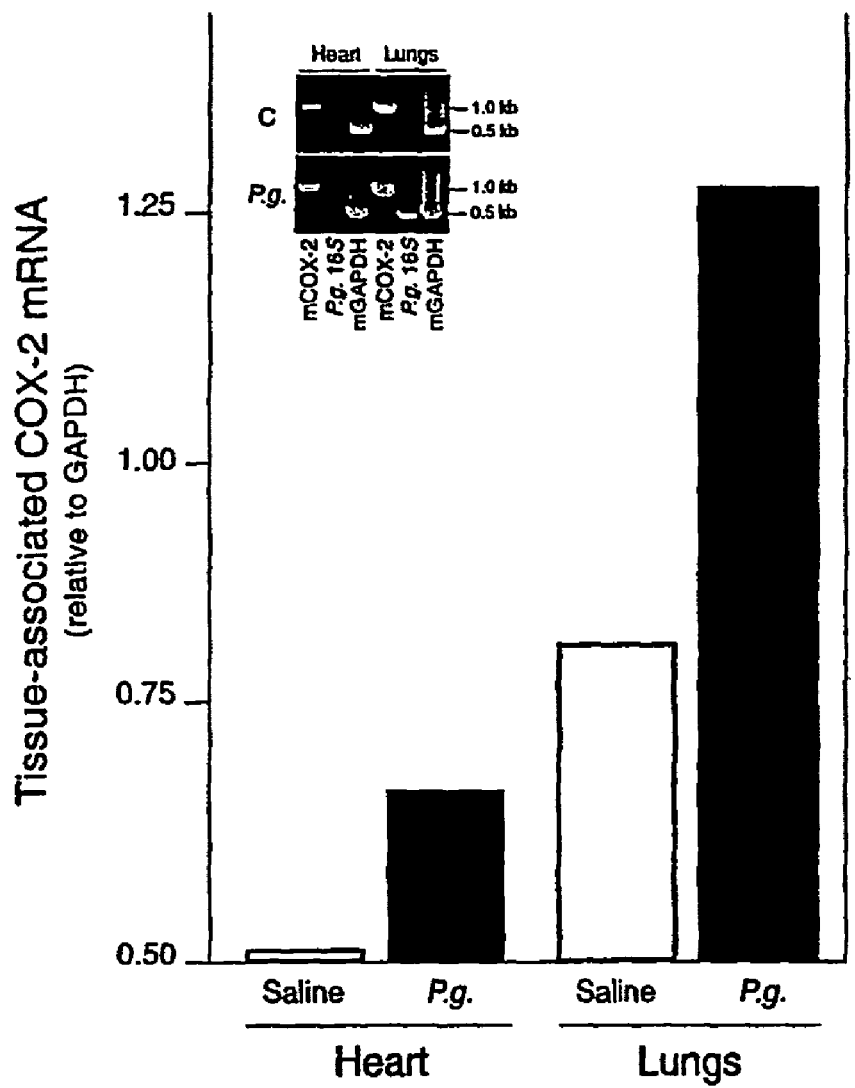

LIPOXIN ANALOGS AND METHOD FOR THE TREATMENT OF PERIODONTAL DISEASE

RELATED APPLICATIONS

This application is a U.S. national phase application under 35 U.S.C. §371 of international application No. PCT/US01/09096 filed Mar. 20, 2001, which international application claims priority to U.S. Provisional Patent Application No. 60/190,656, filed Mar. 20, 2000. International application No. PCT/US01/09096 was filed in English and designated the United States.

GOVERNMENT INTEREST

This invention was made with Government Support under Contract Number DE13499 awarded by the National Institute of Dental & Craniofacial Research. The Government has certain rights in the invention.

FIELD OF THE INVENTION

The present invention relates to lipoxin compounds and COX-2 inhibitors. The present invention also relates to the treatment and prevention of oral inflammation, including gingivitis, periodontitis, and other forms of periodontal disease. Further, the invention relates to methods of preventing systemic diseases beyond the oral cavity that are related to periodontal disease.

BACKGROUND OF THE INVENTION

Periodontal diseases, ranging from gingivitis to more severe forms of periodontitis, are initiated by a bacterial infection followed by a host response that may lead to a highly degenerative oral disease including tooth loss and tissue damage (Page, R. C. (1998) Ann. Periodontol. 3, 108). The current treatments of periodontal diseases, which affect a large percentage of the population, involve primarily the use of compositions containing antimicrobial compounds or various non-steroidal antiinflammatory agents (NSAIDs).

Although bacteria appear to be essential for the causation of periodontitis, progression of periodontal disease is dependent on the host response to pathogens that colonize the tooth surface (Hart, T. C., et al. (1994) J. Periodontol. 65, 521). In turn, periodontal disease can be controlled chemotherapeutically by uncoupling host-mediated destruction rather than reducing the etiological load (Offenbacher, S. et al. (1993) J. Periodontol. 64, 432). Along these lines, a body of evidence has identified the inhibition of $PGE_2$ formation and its presence at gingival sites as being relevant therapeutic interventions. For example, $PGE_2$ generation from gingival homogenates is significantly inhibited by flurbiprofen (ElAttar, T. M. A., et al. (1984) J. Periodontol. 55, 536), and COX-derived eicosanoids in crevicular fluid (CF) are decreased in animals taking flurbiprofen (Smith, M. A., et al. (1993) Infection and Immunity 61, 1453; Offenbacher, S., et al. (1989) J. Periodontal Res. 24, 63). Flurbiprofen also reduced CF-$PGE_2$ levels, gingival inflammation, tooth attachment loss and bone loss, and in some cases resulted in bone gain (Pauletto, N. et al. (1997) J. Can. Dent. Assoc. 63, 824). In humans, flurbiprofen dramatically decreased the CF-$PGE_2$ levels (Abramson, M. M. et al. (1992) J. Periodont. Res. 27, 539). These findings suggest that NSAIDs may exert their pharmacological action of inhibiting COX derived proinflammatory eicosanoids within the periodontium and suggest that novel anti-inflammatory agents might be useful in managing periodontal diseases.

Polymorphonuclear leukocytes (PMN, neutrophils) are the most abundant immune cells recruited to early inflammatory periodontal lesions and are the most numerous host cells within the periodontal tissues (Hart, T. C., et al. (1994) J. Periodontol. 65, 521). The presence of Gram-negative oral pathogens represents the primary etiologic factor, however, the progression of periodontal disease is dependent on the host response to pathogenic bacteria that colonize the tooth surface. Hence, recruitment of PMN followed by aberrant release of inflammatory mediators not only contributes to the onset of periodontal disease and is associated with rapid and widespread tissue destruction (Daniel, M. A., et al. (1996) J. Periodontol. 67,1070), but can also be further amplified by the release of an array of inflammatory mediators by neutrophils within the periodontium.

It is well known that PMN participate in host defense against bacterial infections and are also involved in noxious inflammatory reactions (Weiss, S. J., et al. (1981) J. Clin. Invest. 68, 714; Babior, B. M. (1984) Blood 64, 959). Recruitment of neutrophils to the periodontium contributes to the progression of periodontal disease and to the destruction of periodontal tissues (Page, R. C. (1998) Ann. Periodontol. 3, 108; Daniel, M. A., et al. (1996) J. Periodontol. 67, 1070).

Several inflammatory mediators such as cytokines, chemokines and metalloproteases are associated with periodontal disease (Romanelli, R., et al. (1999) Infect. Immun. 67, 2319; Gainet, J., et al. (1998) Lab. Invest. 78, 755; Assuma, R., et al. (1998) J. Immunol. 160, 403). Other prominent mediators are the arachidonic acid derived products, including leukotriene $B_4$ ($LTB_4$) and prostaglandin $E_2$ ($PGE_2$) (Offenbacher, S. et al. (1986) J. Periodontal Res. 21, 101). Indeed, many of the pathophysiological events that occur in periodontal diseases can be explained to a large extent by the activities of lipid mediators (Solomon, L. M., et al. (1968) J. Invest. Dermatol. 51, 280; Raisz, L. G., et al. (1974) Prostaglandins 8, 377; Klein, D. C., et al. (1970) Endocrinology 86, 1436; Crunkhorn, P., et al. (1969) Br. J. Pharmacol. 36, 216; Collier, J. G., et al. (1972) Br. J. Pharmacol. 44, 374). For example, $LTB_4$, a well appreciated and potent chemoattractant, also initiates the accumulation of leukocytes within inflamed sites, stimulates the release of granule-associated enzymes (Borgeat, P., et al. (1990) Clin. Biochem. 23, 459) and was recently found to stimulate bone resorption (Traianedes, K., et al. (1998) Endocrinology 139, 3178).

Along these lines, PGE2 is a very potent stimulator of bone loss, which is held to be a hallmark of periodontal disease (Zubery, Y., et al. (1998) Infect. Immun. 66, 4158). $PGE_2$ is also well appreciated for its ability to directly mediate vasodilation, increase vascular permeability, enhance pain perception by bradykinin and histamine, alter connective tissue metabolism, and enhance osteodastic bone resorption (Tsai, C.-C. et al. (1998) J. Dentistry 26, 97). The levels of $PGE_2$ are significantly elevated in the crevicular fluid (CF) of patients with periodontal infections, especially localized juvenile periodontitis, when compared to healthy sites. These levels correlate with disease severity and aggressiveness and constitute a reliable indicator of ongoing clinical periodontal tissue destruction (Offenbacher, S., et al. (1984) J. Periodontal Res. 19, 1). CF-$PGE_2$ levels can also be used to predict future acute loss of periodontal attachment (Offenbacher, S., et al. (1986) J. Periodontal Res. 21, 101).

Pathophysiological responses that occur in periodontal diseases, including inflammatory cell recruitment, edema, pain, bone resorption and collagen destruction, can be mediated for the most part by effector molecules originating from the arachidonate cascade (Solomon, L. M. et al. (1968) J. Invest. Dermatol. 51,280; Raisz, L. G., et al. (1974) Prostaglandins 8,377; Klein, D. C., et al. (1970) Endocrinology 86, 1436; Crunkhorn, P., et al. (1969) Br. J. Pharmacol. 36, 216; Collier, J. G., et al. (1972) Br. J. Pharmacol. 44, 374). In particular, considerable evidence has demonstrated the importance of $PGE_2$ in the pathogenesis of periodontal diseases. In vitro, $PGE_2$ increases osteoclast numbers and bone resorption (Lader, C. S., et al. (1998) Endocrinology 139, 3157), decreases proteoglycan synthesis and increases metalloprotease production by cultured chondrocytes (Debrumfernandes, A. J., et al. (1996) Br. J. Pharmacol. 188, 1597). Bone resorption in vivo caused by three periodontal pathogens is mediated in part by $PGE_2$, causing tooth attachment loss and bone loss (Zubery, Y., et al. (1998) Infect. Immun. 66, 4158). Prior to these findings, $PGE_2$ was proposed as a reliable molecular indicator of ongoing periodontal tissue destruction that might be used to predict future acute periodontal attachment loss (Offenbacher, S., et al. (1986) J. Periodontal Res. 21, 101).

Prostaglandin endoperoxide synthase (cyclooxygenase, COX) catalyzes two reactions by which arachidonic acid is converted to $PGH_2$, the common precursor of all prostanoids including $PGE_2$. To date, two COX isoforms are known (Smith, W. L., et al. (1996) J. Biol. Chem. 271, 33157). COX-1 appears to support the levels of prostanoid biosynthesis required for maintaining organ and tissue homeostasis (Smith, W. L., et al. (1996) J. Biol. Chem. 271, 33157; Vane, J. R., et al. (1996) Scand. J. Rheumatol. 102, 9), whereas COX-2 expression appears to be restricted in basal conditions within most tissues and is up-regulated during inflammation or stress in a wide range of tissues (O'Banion, M. K., et al. (1992) Proc. Natl. Acad. Sci. USA 89, 4888; Seibert, K., et al. (1994) Proc. Natl. Acad. Sci. USA 91, 12013; Needleman, P., et al. (1997) J. Rheumatol. 24, 6). The finding that homogenates of inflamed periodontal tissues display an increased $PGE_2$ synthetic capacity when compared to homogenates from healthy tissues suggests an increased COX activity is associated with periodontal tissues (ElAttar, T. M. A. (1976) Prostaglandins 11, 331; Albers, H. K., et al. (1979) Dtsch. Zahnarztl. Z. 34, 440; ElAttar, T. M. A., et al. (1982) Prostaglandins Leukot. Med. 8, 447; ElAttar, T. M. A., et al. (1984) J. Periodontol. 55, 536). Moreover, given the clearly deleterious actions of $PGE_2$ on the integrity of tissues of the periodontal pocket, both the potential involvement of the inducible COX isoform (COX-2) in periodontal disease and potential role of novel lipid mediators are of interest in the pathogenesis of periodontal disease.

Lipoxins (LX) and aspirin-triggered LX (ATL) are arachidonic acid-derived bioactive lipids that are formed by interactions between individual lipoxygenases (LO) and appear to play an important role in downregulating neutrophil responses in inflammation (Serhan, C. N. (1997) Prostaglandins 53, 107). In the nanomolar range, $LXA_4$ and its 15R epimer (15-epi-$LXA_4$) triggered by-aspirin each inhibit fMLP- and $LTB_4$-stimulated PMN adhesion and transmigration and hence represent potential counterregulatory signals operative in the resolution of inflammatory sites (Serhan, C. N. (1997) Prostaglandins 53,107; Serhan, C. N., et al. (1996) FASEB J. 10, 1147; Takano, T., et al. (1997) J. Exp. Med. 185, 1693; Serhan, C. N. et al. (1995) Biochemistry 34, 14609). Like most autacoids and lipid mediators, LX are rapidly generated, act within a local microenvironment, and are rapidly enzymatically inactivated. The roles of LX and ATL roles in vivo, were studied by using metabolically stable LX and ATL analogs that were designed to resist rapid enzymatic inactivation and mimic the in vitro actions of naturally occurring LX and ATL (Serhan, C. N., et al. (1995) Biochemistry 34, 14609).

In addition to confirming the presence of $LTB_4$ and $PGE_2$, (Tsai, C. -C. et al. (1998) J. Dentistry 26, 97), it was shown for the first time that $LXA_4$ is produced by activated neutrophils from LJP patients. It was also shown that $LXA_4$ is present within the crevicular fluid from periodontitis patients with active disease. These results are the first demonstration that LJP peripheral blood neutrophils are in a primed state for LX generation. This in vivo "priming" for up-regulated lipoxin profiles was also observed with neutrophils isolated from asthmatic patients (Chavis, C., et al. (1996) J. Exp. Med. 183, 1633) and can be mimicked in vitro with cytokine-priming of neutrophils from healthy donors (Fiore, S., et al. (1990) J. Exp. Med. 172, 1451).

It was recently reported that $LXA_4$ and ATL analogs reduce leukocyte trafficking stimulated by TNF-α while concomitantly re-orientating the cytokine-chemokine aids towards an anti-inflammatory profile (Hachicha, M., et al. (1999) J. Exp. Med. 189,1923). LX-ATL can thus protect host tissues via multilevel regulation of proinflammatory signals.

Periodontal disease has implications beyond the deleterious effects on oral tissues and structural integrity. Thus, periodontitis represents a potential risk factor for increased morbidity or mortality for several systemic conditions including cardiovascular diseases, pregnancy complications, and diabetes (Page, R. C. (1998) Ann. Periodontol. 3, 108; Garcia, R. I., et al. (1998) Ann. Periodontol. 3, 339). Of great importance in this context, is the finding that the systemic presence of *P. gingivalis* up-regulates the expression of COX-2 (heart and lungs; FIG. 6) which is a marker of on-going inflammation (Herschman, H. R. (1998) Trends Cardiovasc. Med. 8, 145).

The recognition of the endogenous and multifaceted anti-inflammatory role of the lipoxins (Serhan, C. N. (1994) Biochim. Biophys. Acta, 1212, 1; Serhan, C. N. (1997) Prostaglandins 53, 107), combined with the findings that both lipoxin A4 and lipoxin B4 are rapidly deactivated by dehydrogenation (Serhan, C. N.; et al. (1993) Biochemistry, 32, 6313; Maddox, J. F. et al. (1998) FASEB J., 12, 487) or ω-oxidation (Sumimoto, H. et al. (1993) FEBS Lett., 315, 205; Mizukami, Y. et al. (1993) Biochim. Biophys. Acta, 1168, 87; Mizukami, Y. et al. (1994) Eur. J. Biochem, 224, 959), led to the design and synthesis of a number of LX analogs with increased biostability (Serhan, C. N. et al. (1994) Biochemistry, 34, 14609). Several LX analogs of this type were reported to have interesting biological properties and therapeutic potential (Serhan, C. N. et al. (1994) Biochemistry, 34, 14609; Takano, T. et al. (1998) J. Clin. Invest. 101, 819). The use of lipoxin analogs for the treatment and prevention of periodontal disease as well as related systemic diseases, however, has not been described previously.

SUMMARY OF THE INVENTION

The present invention provides new lipoxin analogs, compositions containing these analogs, and methods of using these compounds and compositions for treating and preventing oral inflammation, including gingivitis, periodontitis, and other forms of periodontal disease. In one embodiment, the these new compounds are structural analogs of biostable lipoxin compounds, such as lipoxin $A_4$, lipoxin $B_4$, or other related lipid mediators. Acceptable analogs include, but are not limited to, structural analogs of two series of lipoxins: LXA series ($LXA_4$/15-epi-$LXA_4$) and LXB series ($LXB_4$/15-epi-$LXB_4$).

The lipoxin analogs of the present invention contain four major components: (a) the carboxyl component, (b) the diol component, (c) the tetraene component, and (d) the alcohol component. Each of these components can possess a number of structural variations and still retain the key features necessary for lipoxin activity. Preferred compounds of the present invention generally belong either to the LXA series or the LXB series and can have structural modifications in one or more of the above components.

The compositions containing the lipoxin analogs can be in any form suitable for administration to a human or animal. Preferred forms of the compositions are those that can be administered topically to the oral cavity, for example, solutions, suspensions, dispersions, ointments, creams, pastes, powders, such as tooth powders, toothpastes, gels, lozenges, salve, chewing gum, mouth sprays, pastilles, sachets, mouthwashes, aerosols, tablets, capsules, and floss conjugated with LX analogs.

In another embodiment, the present invention provides methods for treating and preventing oral inflammation, including gingivitis, periodontitis, and other forms of periodontal disease with compositions containing COX-2 inhibitors. For example, compositions containing such compounds as celecoxib, rofecoxib, and valdecoxib, can be administered to a human or animal in manners similar to those for administration of the lipoxin analog containing compositions.

Further, the invention provides methods for preventing systemic diseases beyond the oral cavity that are related to periodontal disease using the compositions containing lipoxin analogs, COX-2 inhibitors, or both. Such diseases include cardiovascular diseases, pregnancy complications, and diabetes.

Therefore, it is an object of the present invention to provide lipoxin analogs, such as LXA and LXB analogs having lipoxin activity.

It is also an object of the present invention to provide compositions comprising lipoxin analogs, such as LXA and LXB analogs having lipoxin activity.

It is a further object of the present invention to provide compositions comprising lipoxin analogs and COX-2 inhibitors.

It is yet another object of the present invention to provide methods for the treatment and prevention of oral inflammation, such as gingivitis, periodontitis, and other periodontal diseases.

It is another object of the present invention to provide methods for the treatment and prevention of aphthous ulcers.

It is a further object of the present invention to provide methods for the treatment and prevention of herpetic stomatitis.

It is an object of the present invention to provide methods for the treatment and prevention of oral inflammation with compositions comprising lipoxin analogs.

It is another object of the present invention to provide methods for the treatment and prevention of oral inflammation with compositions comprising COX-2 inhibitors.

It is yet another object of the present invention to provide methods for the treatment and prevention of oral inflammation with compositions comprising lipoxin analogs and COX-2 inhibitors.

It is an object of the present invention to provide methods for the treatment of systemic diseases associated with periodontal disease.

It is a further object of the present invention to provide methods for the treatment of cardiovascular diseases, pregnancy complications, and diabetes.

It is another object of the present invention to provide methods for the treatment of conditions associated with *Porphyromonas gingivalis*.

BRIEF DESCRIPTION OF THE DRAWINGS

FIG. 1 shows that Activated PMN from LJP patients, but not from asymptomatic controls, generated $LXA_4$.

FIG. 2 demonstrates that *P. gingivalis* elicits leukocyte infiltration in vivo.

FIG. 5 illustrates that the aspirin-triggered LX-analog, 15R/S-methyl $LXA_4$, inhibits *P. gingivalis*-induced $PGE_2$ production in murine air pouch.

FIG. 6 demonstrates that *P. gingivalis* causes systemic up-regulation of COX-2 mRNA.

DETAILED DESCRIPTION OF THE PREFERRED EMBODIMENTS

Figure 3:
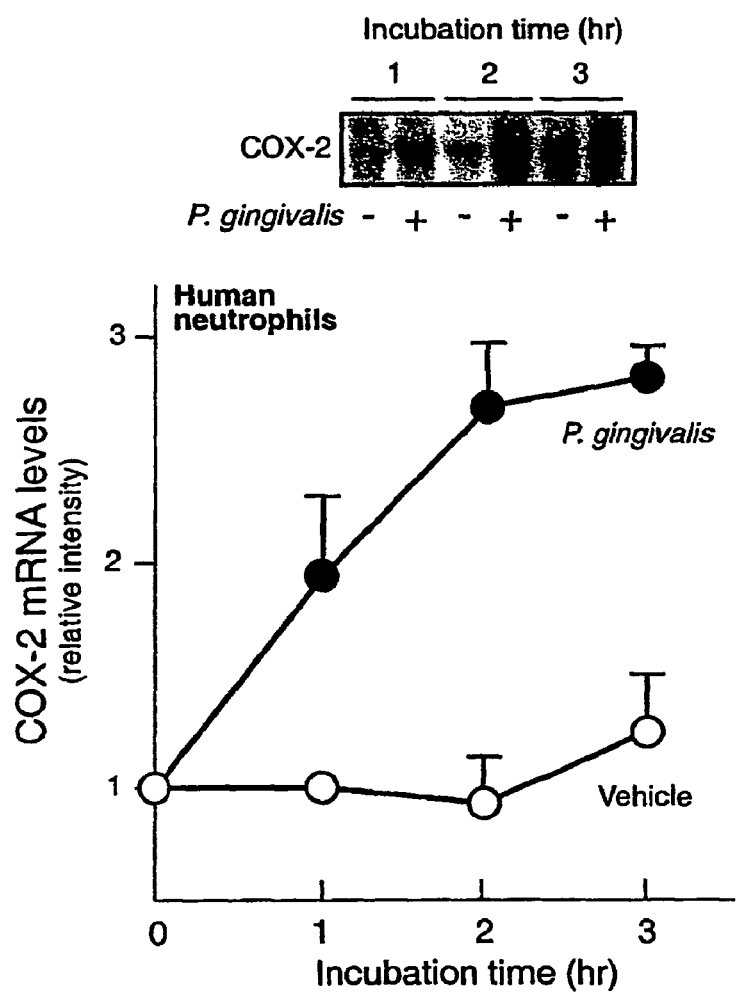
FIG. 3 illustrates that *P. gingivalis* induces COX-2 expression in human PMN.

Generally, the present invention provides new lipoxin analogs, compositions containing these analogs, and methods of using these compounds and compositions for treating and preventing oral inflammation, including gingivitis, periodontitis, aphthous ulcers, herpetic stomatitis, and other forms of periodontal disease. The invention also provides for methods of treating and preventing oral inflammation, including gingivitis, periodontitis, aphthous ulcers, herpetic stomatitis, and other forms of periodontal disease with compositions containing COX-2 inhbitors. Further, the invention provides methods for preventing systemic diseases beyond the oral cavity that are related to periodontal disease using the compositions containing lipoxin analogs, COX-2 inhibitors, or both.

In one embodiment, the present invention provides new lipoxin compounds that are structural analogs of biostable lipoxin compounds, such as lipoxin $A_4$, lipoxin $B_4$, or other related lipid mediator. The term structural analog as used herein means any molecule having the basic structural components of lipoxin compounds. That is compounds containing a carboxyl component, a diol component, a tetraene component, and an alcohol component. These components can be any size and can be joined to one another in any manner. Additionally, these components can contain various substituents or have some of their carbon atoms replaced, for example, by rings or heteroatoms. The compounds of the present invention retain lipoxin activity. However, the compounds of the present invention do not undergo the typical metabolic deactivation of the parent lipoxin compounds. Thus, the in vivo half life of the compounds of the present invention is significantly greater than the half life of the parent compounds. Acceptable analogs include, but are not limited to, structural analogs of two series of lipoxins: LXA series (LXA4 /15-epi-LXA4) and LXB series ($LXB_4$/15-epi-LXB4).

The lipoxin analogs of the present invention contain four major components: (a) the carboxyl component, (b) the diol component, (c) the tetraene component, and (d) the alcohol component. Each of these components can possess a number of structural variations and still retain the key features necessary for lipoxin activity. Preferred compounds of the present invention generally belong either to the LXA series or the LXB series and can have structural modifications in one or more of the above components. The following diagram provides the general formulas for lipoxin compounds of the LXA and LXB series.

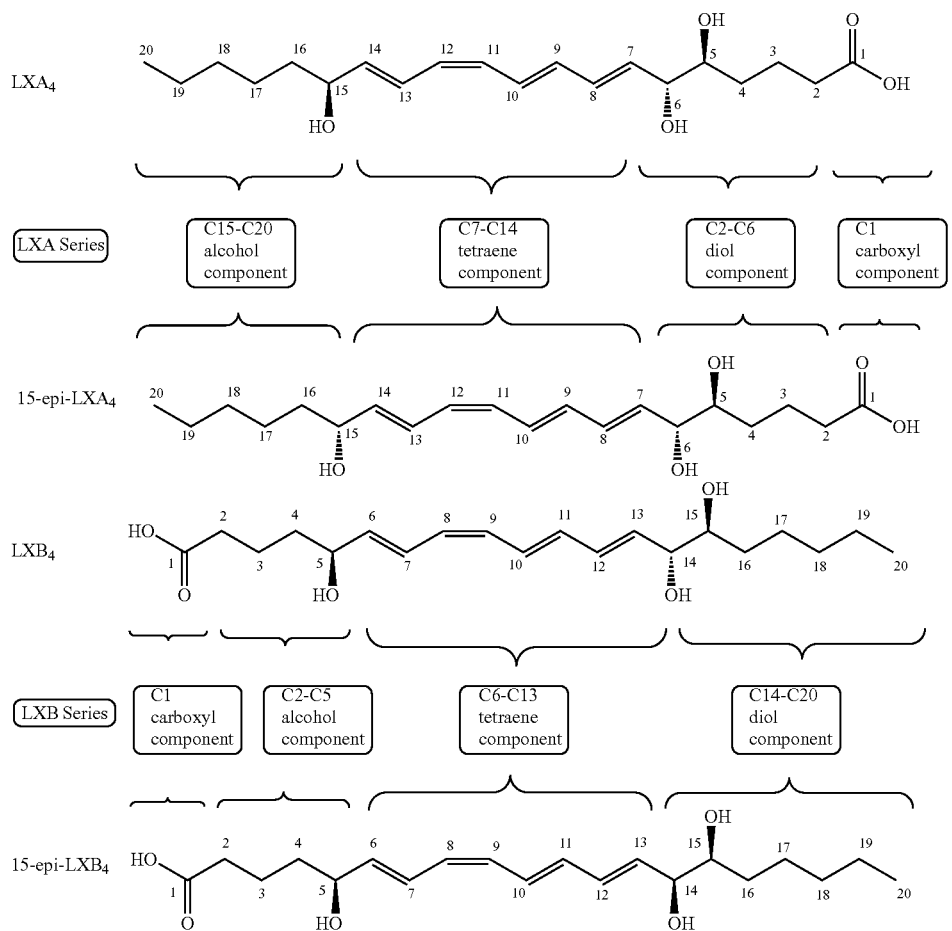

In a preferred embodiment of the present invention, the lipoxin analog a one of the following structures bearing the designated stereochemistry:

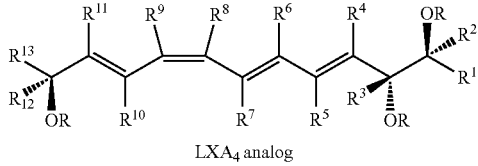

LXA₄ analog

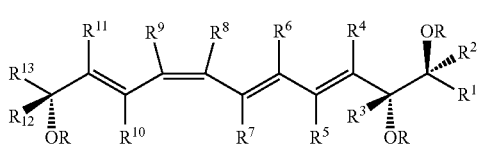

15-epi-LXA₄ analog

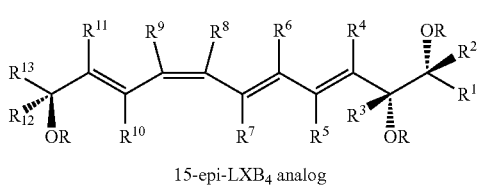

15-epi-LXB₄ analog

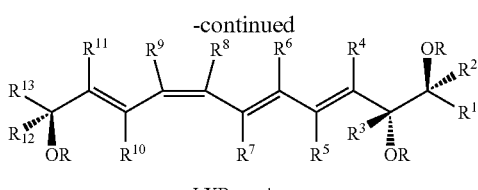

LXB₄ analog

In these structures, the R-groups are independently selected as follows:
R is hydrogen or a straight, branched, cyclic, saturated, or unsaturated alkyl;
$R^1$, $R^2$, $R^{12}$, $R^{13}$ are each independently selected from hydrogen;
straight, branched, cyclic, saturated, or unsaturated alkyl having from 1 to 20 carbon atoms;
substituted alkyl having from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;
substituted aryl or heteroaryl wherein the aryl or heteroaryl is substituted with one or more substituent selected from alkyl, cycloalkyl, alkoxy, halo, aryl, heteroaryl, carboxyl, and carboxamido; and a group Z-Y, wherein Z is a straight, branched, cyclic, saturated, or unsaturated alkyl having from 1 to 20 carbon atoms; substituted lower alkyl wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido; and Y is selected from hydrogen; alkyl; cycloalkyl; carboxyl; carboxamido; aryl; heteroaryl; substituted aryl or heteroaryl wherein the aryl or heteroaryl is substituted with one or more substituents selected from alkyl, cycloalkyl, alkoxy, halo, aryl, heteroaryl, carboxyl, and carboxamido;

$R^3$ is selected from hydrogen; straight, branched, cyclic, saturated, or unsaturated alkyl having from 1 to 20 carbon atoms;

substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;

substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and $R^4$-$R^{11}$ are selected from a group consisting of:
hydrogen;
halo;
straight, branched, cyclic, saturated, or unsaturated alkyl having from 1 to 20 carbon atoms;
substituted alkyl haivng from 1 to 20 carbon atoms, wherein the alkyl is substituted with one or more substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl;
substituted aryl or heteroaryl wherein the aryl or heteroaryl are substituted with one or more substituent selected from alkyl, cycloalkyl, alkoxy, halo, aryl, heteroaryl, carboxyl, and carboxamido;

R, $R^1$-$R^{13}$ may be also connected to form one or more rings containing 3 to 20 carbon atoms, 1 to 6 oxygen atoms or 1 to 6 nitrogen atoms.

A pair selected among the $R^1$-$R^{13}$ groups may also be replaced with a bond that generates a carbon-carbon double or triple bond or a ring.

Examples of preferred compounds of the present invention are shown in Scheme 1. These examples are provided for purposes of illustration and in no way limit the scope of the present invention. Also contemplated as preferred compounds are the compounds shown in Scheme 1 wherein the carbon chains and rings shown in the structures additionally possess substituents selected from halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl.

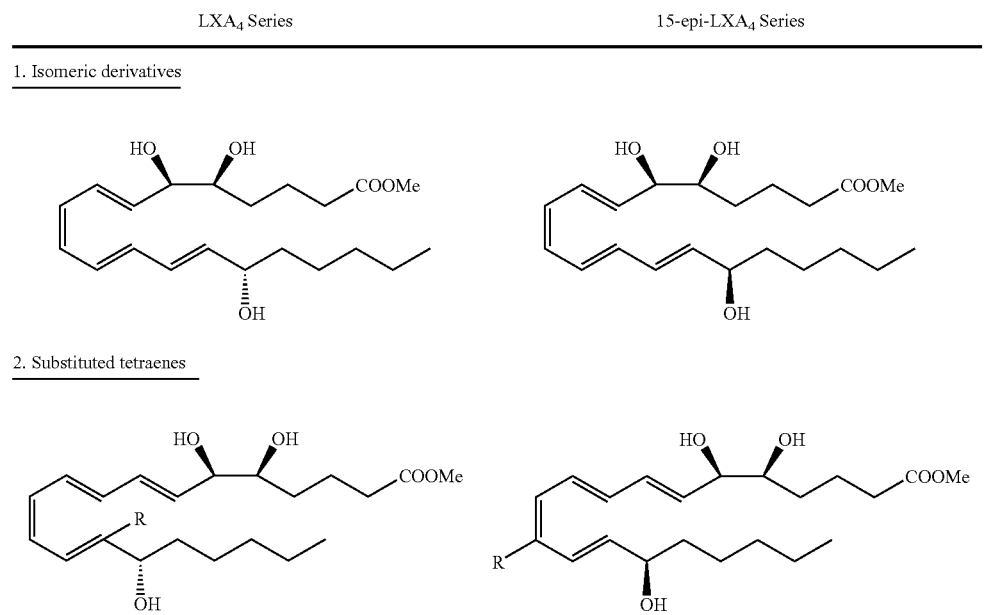

Scheme 1

LXA$_4$ Series      15-epi-LXA$_4$ Series

1. Isomeric derivatives

2. Substituted tetraenes

R = Me, Ph

Scheme 1
3. Ring-substituted tetraenes
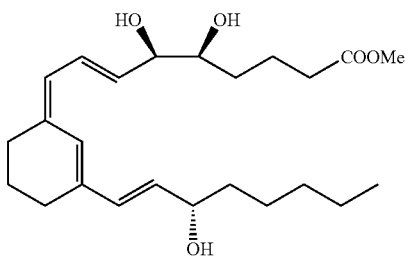 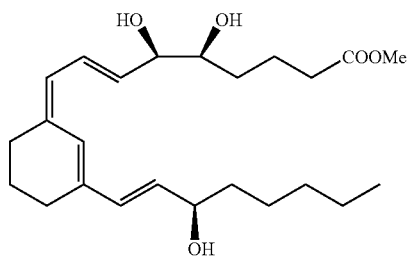
4. Benzo-substituted derivatives
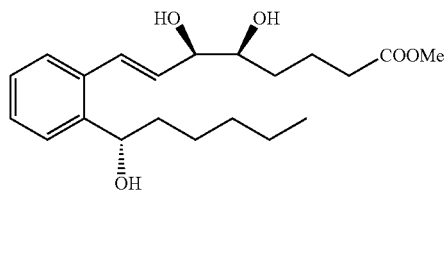 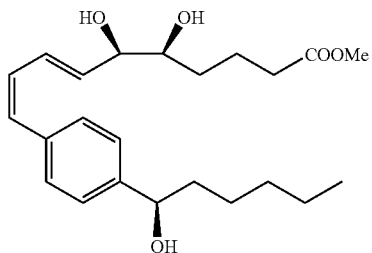
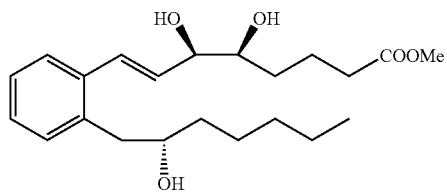 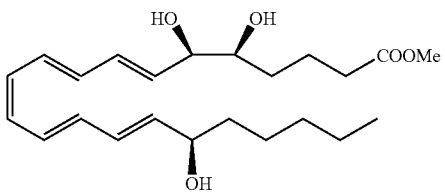
5. Derivatives substituted at the alcohol or diol components
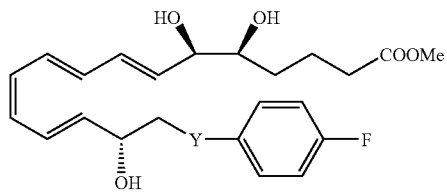 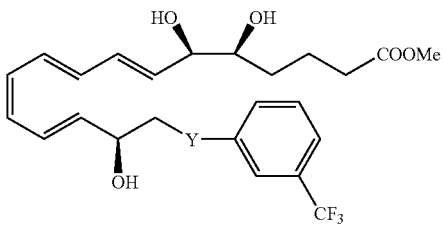
Y = $CH_2$ or O
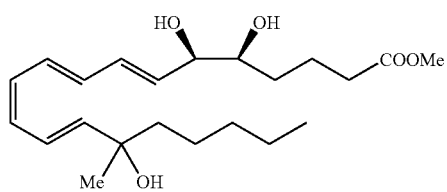 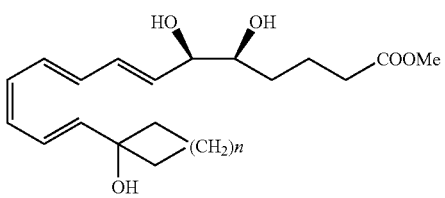
R = Me or $CF_3$      n = 1-10

Scheme 1
6. Hydroxy-replacement derivatives
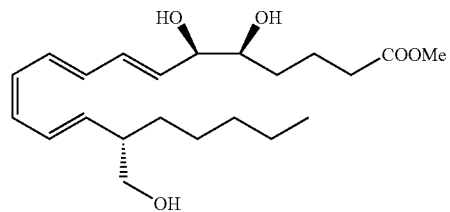
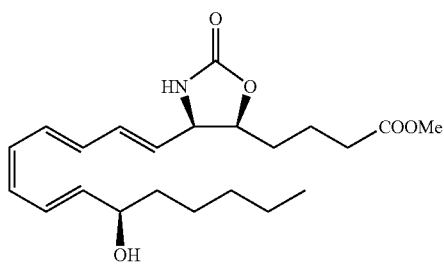
7. Carboxy-replacement derivatives
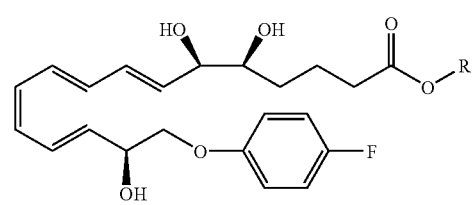
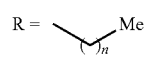
n = 1-10
R = polymeric material
| LXB$_4$ Series | 15-epi-LXB$_4$ Series |
|---|---|
1. Isomeric derivatives
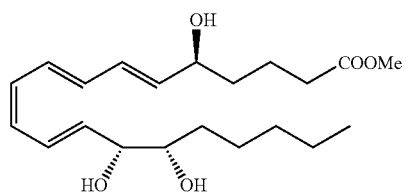
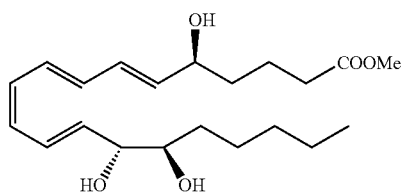
2. Substituted tetraenes
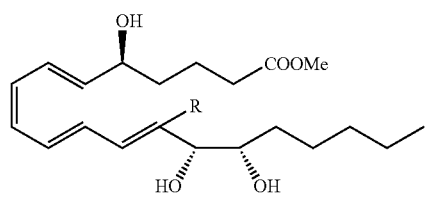
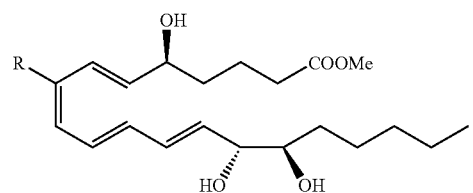
R = Me, Ph
3. Ring-substituted tetraenes
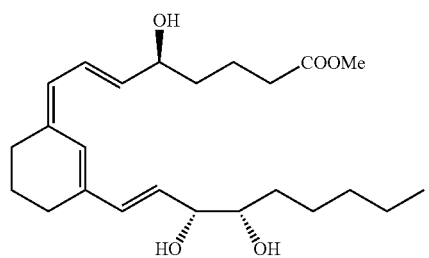

Scheme 1
4. Benzo-substituted derivatives
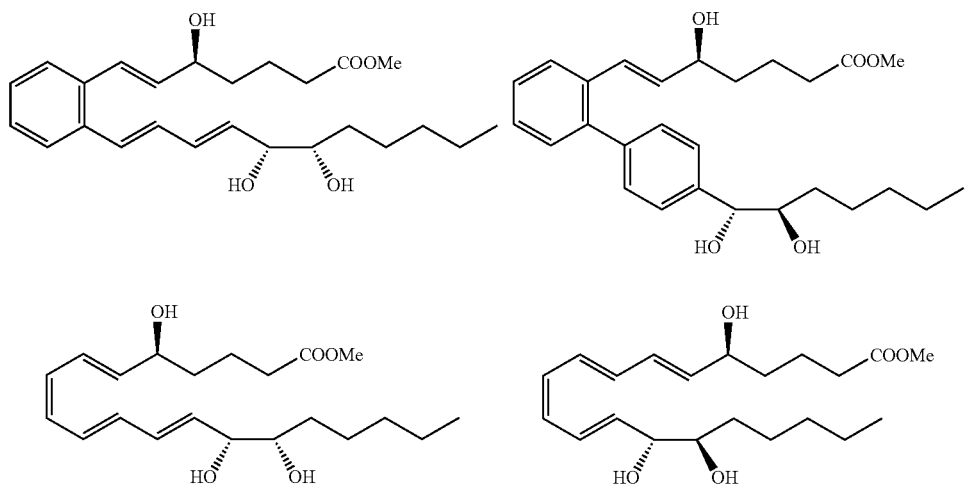
5. Derivatives substituted at the alcohol or diol components
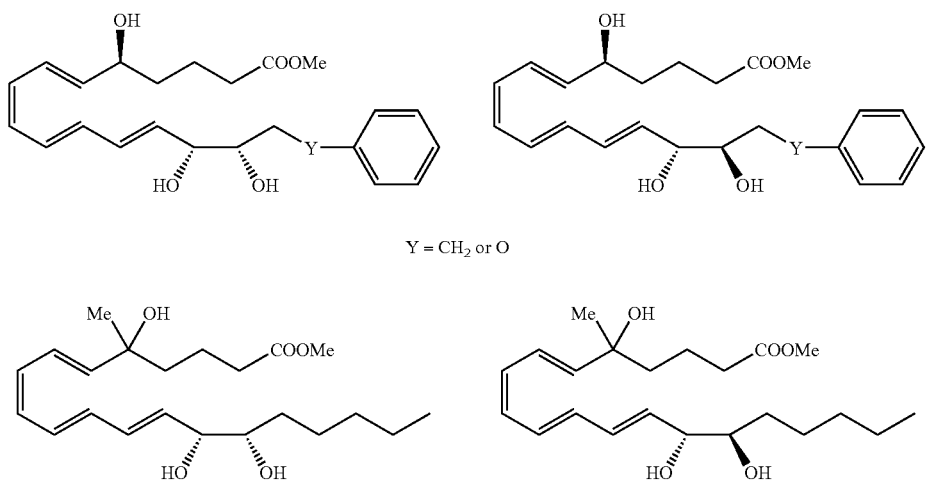
Y = CH$_2$ or O
6. Hydroxy-replacement derivatives
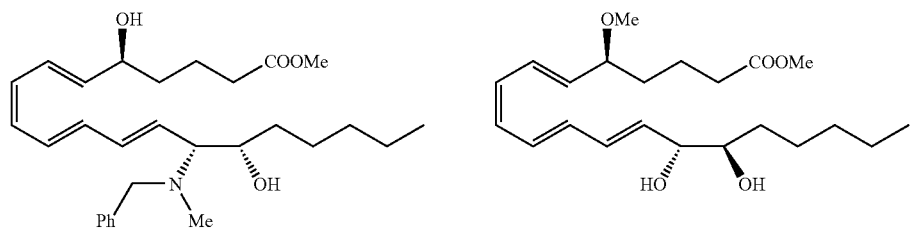

-continued

Scheme 1

7. Carboxy-replacement derivatives

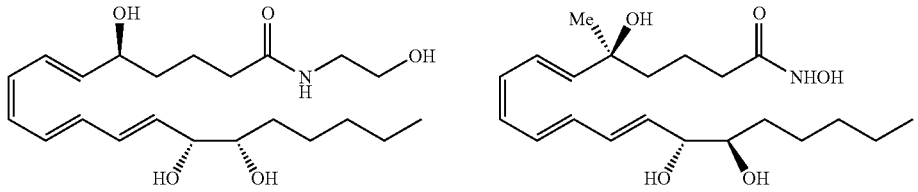

15

The lipoxin analogs of the present invention can be manufactured using conventional methods for producing the parent lipoxin compounds. The reactions necessary to add various functional groups, rings, bonds, and heteroatoms to the present compounds are well within the skill of the ordinary artisan.

In another embodiment, the present invention provides compositions containing these new lipoxin analogs. The new lipoxin analogs of the present invention can be formulated into compositions that are suitable for administration to a human or animal. The compounds can be administered by any suitable means. In general, suitable means of administration include, but are not limited to, topical, transdermal, oral, sublingual, nasal, buccal, rectal, and parenteral (e.g., intravenous, subcutaneous or intramuscular) routes. In addition, the compositions can be incorporated into or covalently attached to polymers for topical use or for sustained delivery. The preferred method of administration is topical, for example, topical delivery to the oral cavity.

The compositions of the present invention can be in any form. These forms include, but are not limited to, solutions, suspensions, dispersions, ointments, creams, pastes, gels, powders, including tooth powders, toothpastes, lozenges, salve, chewing gum, mouth sprays, pastilles, sachets, mouthwashes, aerosols, tablets, capsules, transdermal patch, suppositories, and floss conjugated with LX analogs. Preferred forms of the compositions are those that can be administered topically to the oral cavity. Additionally, the lipoxin analogs of the present invention can be conjugated with or covalently linked to polymers, such as those that are conventionally used for the manufacture of dental floss. The lipoxin analogs can also be incorporated into polymers or biopolymers for the sustained release of the compounds. Further, the lipoxin analogs can be incorporated into liposomes for sustained release delivery.

The compositions of the invention can include other components. These components include, but are not limited to, pharmaceutical carriers, binders, fillers, flavorants, and stabilizers. Additionally, the compositions of the present invention can contain additional active ingredients. For example, the compositions can contain COX-2 inhibitors in addition to the lipoxin analogs. The present invention also provides pharmaceutical compositions comprising COX-2 inhibitors in the absence of the lipoxin analogs.

In yet another embodiment, the present invention provides methods for the treatment and prevention oral inflammation, including gingivitis, periodontitis, aphthous ulcers, herpetic stomatitis, and other forms of periodontal disease with compositions containing the lipoxin analogs of the invention. These methods comprise administering to the patient having such a disease, a composition that comprises a lipoxin analog, a COX-2 inhibitor, or both a lipoxin analog and a COX-2 inhibitor.

The present inventors have identified for the first time by LC/MS/MS-based analyses, that eicosanoids are generated by peripheral blood neutrophils from periodontitis (e.g. LJP) patients. The present inventors have also found that $LXA_4$, $PGE_2$, and $LTB_4$ are present in human CF. Experiments revealed that CF from localized juvenile periodontitis (LJP) patients contain prostaglandin $(PG)E_2$ and 5-lipoxygenase-derived product, leukotriene $B_4$, and the biosynthesis interaction product, lipoxin $(LX)A_4$. Neutrophils from peripheral blood of LJP patients, but not from asymptomatic donors, also generate $LXA_4$ suggesting a role for this immunomodulatory molecule in periodontal disease.

Further, examination of an animal model of leukocyte trafficking and activation of *Porphyromonas gingivalis*, an oral microbe clinically associated with periodontal disease, showed that this microbe potently and rapidly (<4 hr) attracts large numbers of leukocytes, primarily neutrophils (>80%) in vivo. These data indicate that this mediator, $PGE_2$, might originate in part from the infiltrating leukocytes.

*P. gingivalis* also up-regulates the expression of COX-2 from infiltrating leukocytes. In addition, human PMN exposed to *P. gingivalis* also stimulates the expression of COX-2 (FIG. 3). These results indicate that the periodonal pathogens can attract leukocytes in vivo and induce leukocyte-COX-2. In light of the results described herein, the inducible COX isoform expressed in recruited leukocytes (local exudate) may be a major source responsible for production of $PGE_2$ found in the CF of periodontal disease patients (FIGS. 1, 3, and 5).

Given the large number of PMN recruited at inflammatory lesions in periodontal disease, the results described herein identify the PMN as a potential cellular primary target for therapeutic intervention. Metabolically stable lipoxin analogs (LX-ATL) have the potential of blocking PMN infiltration as well as reducing COX-2 derived $PGE_2$ present in gingival tissues. In this regard, topical application of the novel lipoxin analogs of the present invention, or of anti-neutrophil agents as described by Takano (Takano, T., et al. (1998) *J. Clin. Invest.* 101, 819; Hachicha, M. et al. (1999) *J. Exp. Med.* 189, 1923) as well as new selective COX-2 inhibitors as described by (Needleman, P. et al. (1997) *J. Rheumatol.* 24, 6; Herschman, H. R. (1998) Trends Cardiovasc. Med. 8, 145; Golden, B. D. et al. (1999) Rheum. Dis. Clin. North Am. 25, 359), may prove to be advantageous in this disease and associated pain since it could eliminate potential unwanted side-effects (particularly renal effects in the elderly) associated with conventional methods of systemic delivery, such as with nonsteroidal antiinflammatory drugs.

The present inventors have determined that metabolically stable lipid mediators can be used to control host response in periodontal disease and related conditions. Studies confirmed that topical administration of metabolically stable analogs of LX or ATL within the pouch cavity of mice potently blocked *P. gingivalis* induced neutrophil traffic in the dorsal air pouch model and lowered $PGE_2$ levels within exudates.

Together, the above findings identify PMN as an additional and potentially important source of $PGE_2$ in periodontal tissues. Moreover, they provide evidence for a novel protective role for LX in periodontitis, limiting further PMN recruitment and PMN-mediated tissue injury that can lead to loss of inflammatory barriers that prevent systemic tissue invasion of oral microbial pathogens.

Therefore, the present invention provides methods for treating or preventing oral inflammation, such as gingivitis, periodontitis, aphthous ulcers, herpetic stomatitis, and other periodontal diseases by administering compositions containing the novel lipoxin compounds of the present invention. The active ingredient can be delivered over a wide range of doses depending upon the method of delivery and the condition to be treated or, prevented. In general, active doses between about $1 \times 10^{-15}$ grams and $1 \times 10^{-3}$ grams are useful in the present invention. The compositions can be any of those described above and are preferably administered via topical delivery in the oral cavity.

The present invention also provides a method for the treatment or prevention of oral inflammation, including gingivitis, periodontitis, aphthous ulcers, herpetic stomatitis, and other periodontal diseases by administering compositions containing COX-2 inhibitors. Examples of COX-2 inhibitors include, but are not limited to, celecoxib, rofecoxib, and valdecoxib.

Advantageously, the present invention provides methods for treating or preventing oral inflammation, including gingivitis, periodontitis, aphthous ulcers, herpetic stomafitis, and other periodontal diseases by administering compositions containing both lipoxin analogs of the present invention and a COX-2 inhibitor.

In view of their inhibitory impact on neutrophil recruitment and secondarily on $PGE_2$ levels, the lipoxin analogs of the present invention are beneficial to the host not only in the context of periodontitis, but also in a number of diseases which involve excessive PMN responses that can lead to losses in inflammatory barriers and increase invasion of systemic microbes. Blood borne *P. gingivalis* gives significant increases in the murine tissue levels of COX-2 mRNA associated with both heart and lungs, supporting a potential role for this oral pathogen in the evolution of systemic events.

The concept that a local infection by *P. gingivalis* may have a systemic impact on the status of the immune system, is further substantiated by the finding that *P. gingivalis* injected in the air pouch up-regulates COX-2 mRNA levels in the lung-associated tissues. In view of these results, an effective treatment of periodontal conditions is likely to have a beneficial impact on the prognosis of a number of systemic diseases.

Thus, the present invention is also related to methods for treating systemic diseases that are related to periodontal disease, such as cardiovascular diseases, pregnancy complications, and diabetes. These methods comprise administering to the patient having such a disease, a composition that comprises a lipoxin analog, a COX-2 inhibitor, or both a lipoxin analog and a COX-2 inhibitor.

EXAMPLES

The present invention is further illustrated and supported by the following examples. However, these examples should in no way be considered to be further limit the scope of the invention. To the contrary, one having ordinary skill in the art would readily understand that there are other embodiments, modifications, and equivalents of the present invention without departing from the spirit of the present invention and/or the scope of the appended claims.

Example 1

Identification of Eicosanoids From Human Poly-Morphonuclear Leukocytes in Juvenile Periodontitis It was previously suggested that localized juvenile periodontitis (LJP) patients present altered lipid metabolism, including the 15-LO pathway (Noguchi, Z., et al. (1988) Prostaglandins Leukotrienes and Essential Fatty Acids 33, 137). Therefore, we evaluated the capacity of peripheral blood PMN from LJP patients and periodontal disease from age, sex, and race matched controls to produce 5- and 15-LO-derived eicosanoids, as well as the LO interaction product $LXA_4$.

Human polymorphonuclear leukocytes (PMN) from healthy volunteers and patients with juvenile periodontitis were obtained by gradient centrifugation of heparinized fresh venous blood using the method of Böyum (Böyum, A. (1968) Scand. J. Clin. Lab. Invest. Suppl. 21, 77). Resulting granulocyte suspensions contained fewer than 0.2% monocytes as determined by esterase staining, and viability was greater than 96% as determined by trypan blue dye exclusion.

Freshly isolated PMN ($5 \times 10^6$ cells) were suspended in 0.5 ml Hank's buffered saline with 1.6 mM $Ca^{2+}$ and incubated with A23187 (4 μM) at 37° C. for 20 minutes. The incubations were stopped with two volumes of cold methanol and kept at −20° C. overnight. Protein precipitates were pelleted by centrifugation and washed twice with methanol. The supernatants were pooled, and the eicosanoids were extracted with Extract-Clean solid phase cartridges (500 mg $C_{18}$, Alltech Associates Inc., Deerfield, Ill.), using $PGB_2$ ($[M-H]^-$=m/z 333) as an internal standard for extraction recovery calculations (Takano, T., et al. (1998) J. Clin. Invest. 101, 819). The methyl formate fractions were taken to dryness with a gentle stream of nitrogen and suspended in mobile phase for LC/MS/MS analyses. LC/MS/MS was performed employing an LCQ (Finnigan MAT, San Jose, Calif.) quadrupole ion trap mass spectrometer system equipped with an electrospray ionization probe. Samples were injected into the HPLC component, comprised of a SpectraSYSTEM P4000 (Thermo Separation Products, San Jose, Calif.) quaternary gradient pump, a LUNA C18-2 (150×2 mm, 5 μm) column, and a SpectraSYSTEM UV2000 (Thermo Separation Products, San Jose, Calif.) UV/VIS absorbance detector. The column was eluted isocratically for 20 minutes with methanol/water/acetic acid (65:34.99:0.01, v/v/v) at 0.2 ml/min, followed by a 20 minute linear gradient to methanol/acetic acid (99.99:0.01, v/v), and into the electrospray probe. The spray voltage was set to 5-6 kV and the heated capillary to 250° C. Eicosanoids were quantitated by selected ion monitoring (SIM) for analyte molecular anions (e.g. $[M-H]^-$=m/z 351.5 for $LXA_4$ and m/z 335.5 for LTB$_4$). Product ion mass spectra (MS/MS) were also acquired for definitive identification of the compounds.

Gingival CF from juvenile periodontitis patients was collected on periostrips (Ebersole, J. L. et al. (1980) J. Periodontal Res. 15, 621). The periostrips were placed in 50 µl of phosphate buffered saline with 20% Tween 20 and LXA$_4$, LTB$_4$, and PGE$_2$ were quantitated by specific ELISA analyses (Neogen Corporation, Lexington, Ky.). As determined by LC/MS/MS, recoveries of known amounts of LXA$_4$, LTB$_4$, and d$_4$-LTB$_4$ from periostrips were linear over a 100 pg to 10 ng range, with 82.7% ($r^2$=0.996), 85.6% ($r^2$=0.999), and 72.7% ($r^2$=0.996) recovery, respectively.

PMN from both healthy donors and LJP patients, incubated with arachidonic acid, produced both 5- and 15-HETE from exogenous substrate, which were identified by LC/MS/MS and chiral phase HPLC analyses indicating that the alcohol at carbon 15 position of 15-HETE was in the S configuration, suggesting involvement of a 15-lipoxygenase. On the other hand, activated PMN produced LTB$_4$ and its omega-oxidation metabolite 20-OH-LTB$_4$, in addition to 5- and 15-HETE generated from endogenous sources of arachidonic acid (Table 1).

TABLE 1

Eicosanoids formed by activated peripheral blood PMN*

| | LTB$_4$ ng | 20-OH-LTB$_4$ ng | 5-HETE ng | 15-HETE ng |
|---|---|---|---|---|
| Non-periodontal disease donor | 29 | 76 | 0.51 | 0.11 |
| LJP-001 | 11 | 42 | 0.00 | 0.46 |
| LJP-002 | 28 | 103 | 0.38 | 0.04 |
| LJP-003 | 24 | 150 | 0.05 | 0.52 |
| LJP-004 | 24 | 63 | 4.10 | 0.65 |

*PMN (5 × 10$^6$) from non-periodontal disease donors and LJP patients were isolated and suspended in 0.5 ml Hank's with 1.6 mM Ca$^{2+}$ and incubated (20 min., 37° C.) in parallel with A23187 (4 µM). Samples were prepared for LC/MS/MS, and eicosanoids were identified by signature MS and MS/MS ions, and the quantifies were calculated from the recovery of the internal standard (PGB$_2$). Values for activated PMN from non-periodontal disease donors are representative and consistent with those obtained for at least n = 6 healthy donors.

Activated PMN from LJP patients, but not from controls, namely asymptomatic individuals without evidence of clinically documented periodontal disease, also generated LXA$_4$ (FIG. 1). The presence of a number of enzymes involved in the production of lipid mediators, including 5-, 12-, 15-LO, COX-1 and COX-2, in leukocytes from periodontitic patients was also confirmed by RT-PCR. CF from periodontal disease, specifically patients with LJP were analyzed for the presence of key eicosanoids, including LXA$_4$, PGE$_2$ and LTB$_4$ from each major class of eicosanoid mediators. LXA$_4$ was also present in the crevicular fluid of patients (Table 2), suggesting a potential role for this immunomodulatory molecule (Serhan, C. N. (1997) Prostaglandins 53, 107) in the local inflammatory sequelae observed within the periodontium of patients with periodontal diseases. Moreover, both the proinflammatory COX and the 5-LO derived eicosanoids, PGE$_2$ and LTB$_4$ respectively, were also demonstrated in the CF (Tsai, C.-C. et al. (1998) J. Dentistry 26, 97).

TABLE 2

Crevicular fluid from LJP patients contain eicosanoids*.

| | PGE$_2$ | LTB$_4$ | LXA$_4$ |
|---|---|---|---|
| Amount: | 10.2 ± 0.3 | 8.7 ± 0.2 | 1.7 ± 1.0 |
| Ratio: | 6.2 | 5.1 | 1 |

*Values represent the mean ± SEM for 10 determinations from 4 LJP patients (pg/µl-CF sample) from specific ELISA analyses. Ratios (relative to LXA$_4$) are indicated for each eicosanoid. Average CF volume: 0.70 ± 0.16 µl (mean ± SEM; n = 10).

Example 2

Recruitment of Murine Leukocytes Into Air Pouches by *Porphyromonas gingivalis*

PMN recruitment to gingival sites and high PGE$_2$ levels are associated with periodontal disease (Offenbacher, S. et al. (1984) J. Periodontal Res. 19, 1; Noguchi, Z., et al. (1988) Prostaglandins, Leukotrienes and Essential Fatty Acids 33, 137). We therefore sought to determine the impact that *P. gingivalis* may have in vivo on leukocyte trafficking and COX-2 expression. To this end, we used a murine air pouch model to assess leukocyte infiltration and activation.

Six to eight week old male BALB/c mice were obtained from Taconic Farms (Germantown, N.Y.). Air pouches were raised on the dorsum by s.c. injection of 3 ml of sterile air on day 0 and day 3, and all experiments were carried out on day 6 (Sin, Y. M., et al. (1986) Ann. Rheum. Dis. 45, 873). Individual air pouches (one per mouse) were injected with either vehicle alone (0.1% ethanol), with 10 µg 15-R/S-methyl-LXA$_4$-me or with 10 µg 15-epi-16phenoxy-LXA$_4$-me, followed by 500 µl of sterile PBS or ~10$^5$ cells of *P. gingivalis* strain A7436 (OD$_{600}$ 0.9-1.0) originally obtained from the CF of a patient diagnosed with periodontitis. Mice were sacrificed 4 hr post-injection and individual air pouches were lavaged three times with sterile PBS (3 ml for each lavage) (Sin, Y. M. et al. (1986) Ann. Rheum. Dis. 45, 873; Hachicha, M., et al. (1999) J. Exp. Med. 189, 1923). The exudates were centrifuged at 2000 rpm (5 min) and supernatants were taken and stored at −20° C. Cell pellets were suspended in PBS (200 µl) for enumeration by light microscopy, and 50 µl of each cell suspension were mixed with 150 µl 30% BSA and then centrifuged onto microscope slides at 500 RPM for 5 min using a cytospin centrifuge, air dried, and stained with Giemsa-Wright to identify individual cell type. Air pouch exudates were assessed for PGE$_2$ using an enzyme immunoassay (EIA) kit (Cayman Chemical Co., Ann Arbor, Mich. [cross-reactivities in the PGE$_2$ EIA kit were <0.04% for 6-keto PGF$_{1\alpha}$ and <0.01% for LTB$_4$, thromboxane B$_2$ and arachidonic acid]). For intravenous procedures, 100 µl of the same *P. gingivalis* suspension were injected in the orbital plexus.

In these studies, *P. gingivalis* elicited a massive leukocyte infiltration into the air pouches. Approximately 10 million leukocytes were enumerated in the *P. gingivalis*-injected air pouch exudates (FIG. 2). This cell infiltration represents approximately three times more leukocytes than in air pouches injected with murine TNFα (Hachicha, M., et al. (1999) J. Exp. Med. 189, 1923). These inflammatory exudates were comprised predominantly of neutrophilic infiltrate that represented ~80-85% of the total leukocytes recruited at 4 h. The remainder of the recruited leukocytes were mononuclear cell infiltrate ~15-20%, consistent with earlier findings (Hachicha, M., et al. (1999) J. Exp. Med. 189, 1923), yet suggesting that *P. gingivalis* stimulates greater numbers of PMN in this model than murine TNFα. Also, in the present experiments, relatively few leukocytes were present in PBS-injected air pouch lavages. These results showed that *P. gingivalis* represents a potent stimulus for the recruitment of leukocytes, predominantly neutrophil infiltrate, within a localized site or cavity (i.e. dorsal pouch).

Example 3

Induction of COX-2 by *Porphyromonas gingivalis*

It is well known that COX-2 is induced in human PMN by a number of inflammatory mediators, including *Escherichia coli* (Pouliot, M., et al. (1998) FASEB J. 12, 1109). We determined that *P. gingivalis* also directly stimulates COX-2 expression in PMN freshly isolated from peripheral blood.

Total RNA isolation and hybridization were performed essentially as in Pouliot, M., et al. (1998) FASEB J. 12, 1109. Briefly, filters were hybridized with human or mouse COX-2 cDNA probes which were synthesized by reverse-transcription polymerase chain reaction (RT-PCR). The primers used were: 5'-GCT GAC TAT GGC TAC AAA AGC TGG-3' (SEQ ID NO. 1) and 5'-ATG CTC AGG GAC TTG AGG AGG GTA-3' (SEQ ID NO. 2) for human COX-2; 5'-AAC TCC CAT GGG TGT GAA GGG A-3' (SEQ ID NO. 3) and 5'-CCA AAG ATA GCA TCT GGA CGA G-340 (SEQ ID NO. 4) for mouse COX-2. Integrity of the RNA and equal loading on agarose/formaldehyde gels were verified by hybridization with glyceraldehyde-3-phosphate dehydrogenase (GAPDH). The observed COX-2 mRNA band was approximately 4.6 kb. Autoradiograms were scanned using an Epson 636 scanner (Epson America). For RT-PCR analyses, total RNA was extracted by homogenizing tissues in Trizol (Gibco-BRL, Grand Island, N.Y.), according to the manufacturer's instructions. One pg of total RNA was used in each reaction using Titan One tube RT-PCR (Roche Molecular Biochemicals, Indianapolis, Ind.). Reverse transcription (RT) and polymerase chain reaction (PCR) were sequentially performed according to the following profile: 50° C. for 30 min for RT, then 94° C. for 30 s; 60° C. for 30 s; 72° C. for 1 min; repeated 35 times for PCR, followed by a final extension at 72° C. for 10 min. Primers used for mouse COX-2 were identical to those mentioned above and the expected PCR product was 1.0 kb in length. For the detection of *P. gingivalis* in mouse tissues, primers specific for 16S ribosomal RNA of the bacteria (Genbank accession number: L16492) were utilized: 5'-GGC AGG CGG AAT TCG TGG TGT A-3' (SEQ ID NO. 5) and 5'-GAT GTA AGG GCC GTG CTG ATT TGA-3' (SEQ ID NO. 6). PCR products, both for *P. gingivalis* ribosomal RNA and mouse GAPDH, had an expected length of 0.5 kb. Samples were migrated on 1% agarose gel containing ethidium bromide and photographs of the gels were taken under UV illumination. All densitometry analyses were performed using the National Institute of Health Image program, which can be found at the following web site: (http://rsb.info.nih.gov) and is incorporated by reference herein.

Indeed, *P. gingivalis* increased the levels of COX-2 mRNA in a time-dependent fashion when compared to that from vehicle-treated PMN (FIG. 3). An increase was first observed at 1 hr and COX-2 mRNA levels further increased in presence of the bacteria, compared to vehicle alone, for up to 3 hr. The expression of COX-2 in leukocytes which migrated into the air pouch cavity, as described in Example 2, was also determined. As assessed by northern blot, COX-2 expression was up-regulated in these activated leukocytes (see FIG. 5 insert). These results indicated that oral pathogens associated with periodontal diseases such as *P. gingivalis* up-regulate COX-2 expression in human PMN and in infiltrating leukocytes. These results provide direct support for the hypothesis that neutrophils, which constitute the first and most numerous inflammatory cell type migrating to local gingival tissues in periodontal disease, may constitute a previously unappreciated source of COX-2 derived eicosanoids, including $PGE_2$, in the periodontium.

Example 4

LX Analogs Inhibit *Porphyromonas gingivalis*-Elicited Leukocyte Infiltration and Trafficking of COX-2 In Vivo In view of the finding that $LXA_4$ and aspirin-triggered LX (LX-ATL) analogs reduce leukocyte trafficking stimulated by TNFα in the murine air pouch (Hachicha, M. et al. (1999) J. Exp. Med. 189, 1923) and because PMN are the most abundant inflammatory cells recruited to pathogen-infected gingival sites in periodontal disease, we evaluated the impact of the metabolically stable LX-ATL analogs 15-R/S-methyl $LXA_4$ and 16-phenoxy $LXA_4$ on the recruitment of leukocytes into murine air pouches by P. gingivalis.

Figure 4:
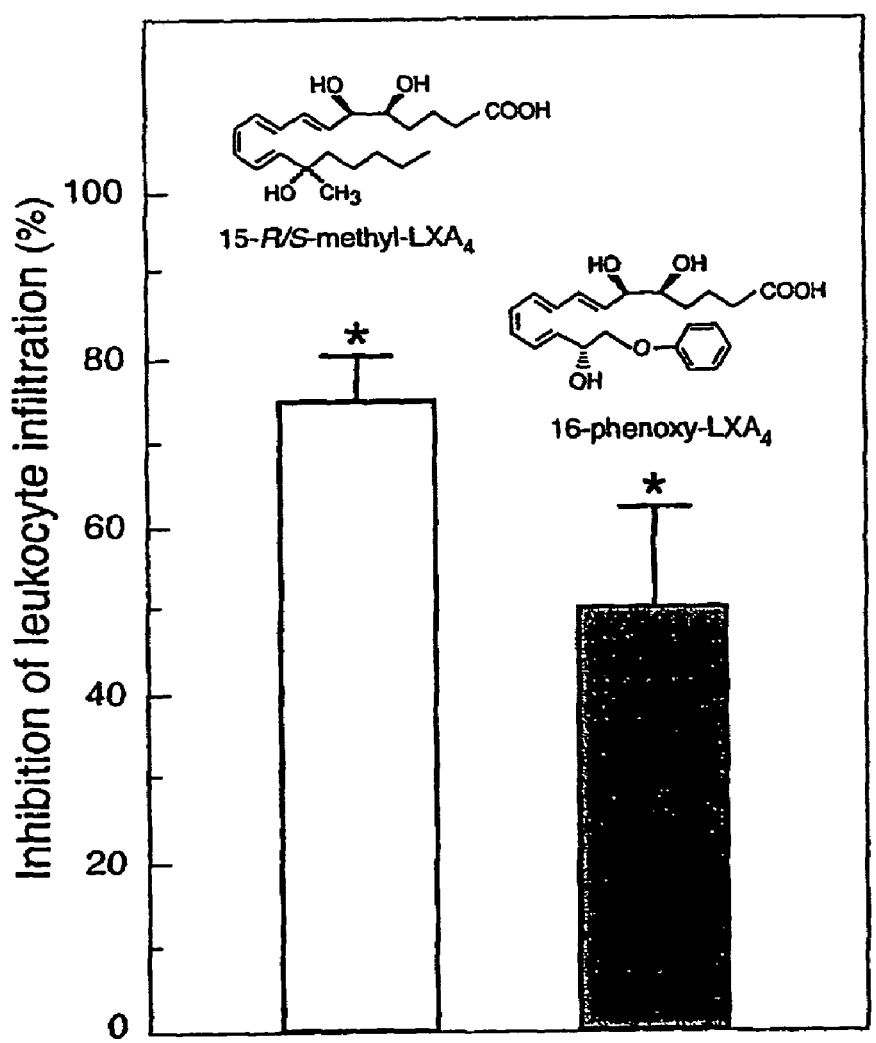
FIG. 4 shows that $LXA_4$ analogs inhibit leukocyte infiltration in vivo.

Air pouches (see Example 2) were injected either with vehicle, with 15-R/S-methyl $LXA_4$ (10 µg/pouch), or with 16-phenoxy $LXA_4$ (10 µg/pouch) then injected with viable *P. gingivalis*, as in FIG. 4. In these experiments, LX-ATL analogs dramatically reduced the recruitment of leukocytes into the air pouches exudate. Both analogs were essentially equipotent inhibitors of leukocyte infiltration, decreasing leukocytes within the exudates by up to 75% with as little as 10 µg application (FIG. 4).

Since $PGE_2$ is associated with loss of attachment and bone loss in periodontal disease (Offenbacher, S., et al. (1992) J. Periodontal Res. 27, 207), we determined $PGE_2$ levels in the air pouch exudates. Air pouches injected with *P. gingivalis* (see Example 2) contained elevated $PGE_2$ levels compared to those of vehicle-injected air pouches (FIG. 5). *P. gingivalis* stimulated the production of nanogram levels of $PGE_2$ in the exudates, which paralleled the up-regulated expression of COX-2 in infiltrating leukocytes (FIG. 5, insert). The ATL analog 15-R/S-methyl $LXA_4$, inhibited $PGE_2$ production generated in response to the oral pathogen, decreasing $PGE_2$ levels in the exudates by as much as 75%. This inhibition in $PGE_2$ levels paralleled the decrement in leukocytes observed within the exudate (FIG. 4). Also, the expression of COX-2 was evaluated in exudate leukocytes. 15-R/S-methyl $LXA_4$ within the air pouch decreased the overall expression of COX-2 in exudates (FIG. 5, insert). These results indicate that *P. gingivalis* induces the in vivo expression of COX-2 within infiltrating leukocytes as well as the production of $PGE_2$. Moreover they indicate that LX-ATL are potent regulators of $PGE_2$ production in air pouch exudates as a consequence of inhibiting leukocyte transmigration and reducing COX-2 mRNA levels.

Given the large number of PMN recruited at inflammatory lesions in periodontal disease, these results identify the PMN as a potential cellular primary target for therapeutic intervention. LX-ATL have the potential of blocking PMN infiltration as well as reducing COX-2 derived $PGE_2$ present in gingival tissues.

These findings support the concept that $LXA_4$, which has an immunomodulatory action, may be involved in the regulation of the local acute inflammatory responses in periodontal disease. Moreover, these results indicate that LX-ATL analogs, which are topically active (Takano, T. et al. (1997) J. Exp. Med. 185, 1693), are potent inhibitors of *P. gingivalis*- elicited leukocyte migration towards a site of infection. These analogs also concomitantly reduce the overall levels of COX-2 mRNA associated with inflammatory exudates, which was accompanied by a decreased production of $PGE_2$. Overall, these results provide evidence for a potential role for lipoxins in the host defense mechanisms evoked by *P. gingivalis*. Based on these findings, it can also be expected that lipoxin analogs would have useful for the treatment and prevention of periodontal disease.

Example 5

Systemic Up-Regulation of COX-2 Expression by *Porphyomonas gingivalis*.

Because COX-2 expression is up-regulated in acute and chronic inflammatory situations (Herschman, H. R. (1998) Trends Cardiovasc. Med. 8, 145), we determined the systemic impact that *P. gingivalis* may have by evaluating selected organ-associated levels of COX-2 mRNA. It should be noted that COX-2 was initially identified as an early response gene (Herschman, H. R. et al. (1993) J. Lipid Mediat. 6, 89).

A suspension of *P. gingivalis*, or an equivalent volume of sterile PBS, was injected in the orbital plexus of the mice. After 4 hr, animals were sacrificed and COX-2 mRNA levels were determined in the heart and lungs. Intravenous injection of *P. gingivalis* caused a significant increase in the levels of COX-2 mRNA associated with the heart and lungs (FIG. 6). *P. gingivalis*-specific 16S ribosomal RNA (Example 3) was readily observed in the heart and lungs from mice injected with the oral pathogen, and was absent in tissue samples from the PBS-injected animals (FIG. 6, insert).

These findings show that the systemic presence of *P. gingivalis* up-regulates expression of COX-2 (heart and lungs; FIG. 6), a marker of on-going inflammation (Herschman, H. R. (1998) Trends Cardiovasc. Med. 8, 145). The concept that a local infection by *P. gingivalis* may have a systemic impact on the status of the immune system was further substantiated by results obtained in pilot studies, where *P. gingivalis* injected in the air pouch unregulated COX-2 mRNA levels in the lung-associated tissues.

In view of these results, an effective treatment of periodontal conditions is likely to have a beneficial impact on the prognosis of a number of systemic diseases. $LXA_4$ and ATL analogs reduce leukocyte trafficking stimulated by $TNF\alpha$ while concomitantly re-orientating the cytokine-chemokine axis towards an anti-inflammatory profile (Hachicha, M. et al. (1999) J. Exp. Med. 189, 1923). LX-ATL can thus protect host tissues via multilevel regulation of proinflammatory signals. In view of their inhibitory impact on neutrophil recruitment and secondarily on $PGE_2$ levels, LX-ATL may be beneficial to the host not only in the context of periodontitis, but also in a number of diseases which involve excessive PMN responses that can lead to losses in inflammatory barriers and increase invasion of systemic microbes.

These results demonstrate the capacity of *P. gingivalis* to up-regulate COX-2 expression systemically in a murine model, supporting a potential role for this oral pathogen in the evolution of systemic events. Indeed, evidence is accumulating to support the notion that periodontal disease may affect, and worsen, systemic diseases such as coronary heart disease, preterm labor and diabetes mellitus (Page, R. C. (1998) Ann. Periodontol. 3, 108) and that brushing or trauma to an inflamed gingival site can lead to septicemia (Silver, J. G., et al. (1979) J. Clin. Priodontol. 6, 33).

Therefore, the present invention, by controlling PMN responses in periodontitis also offers a novel approach for the treatment and prevention of a variety of systemic diseases.

We claim:

1. A method of treating a periodontal disease in a human or animal comprising administering to the human or animal a therapeutically effective amount of a composition comprising a compound which is a structural analog of lipoxin $A_4$ ($LXA_4$), lipoxin $B_4$ ($LXB_4$), 15-epi-lipoxin $A_4$ (15-epi-$LXA_4$) or 15-epi-lipoxin $B_4$ (15-epi-$LXB_4$).

2. The method according to claim 1, wherein the compound is:

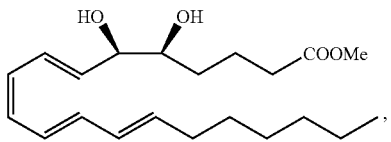

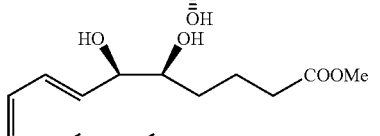

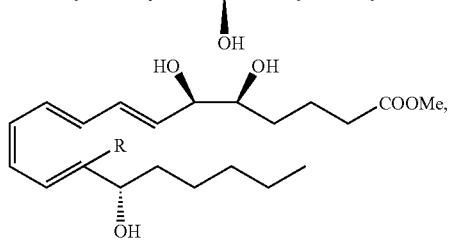

-continued

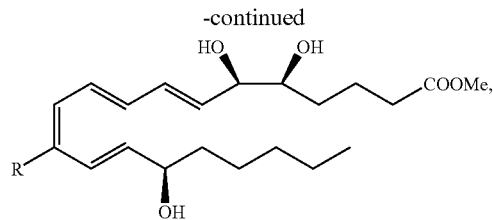

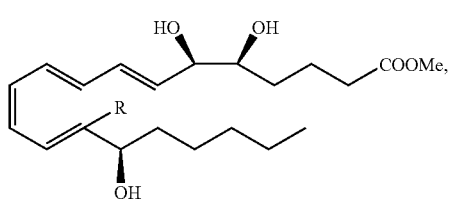

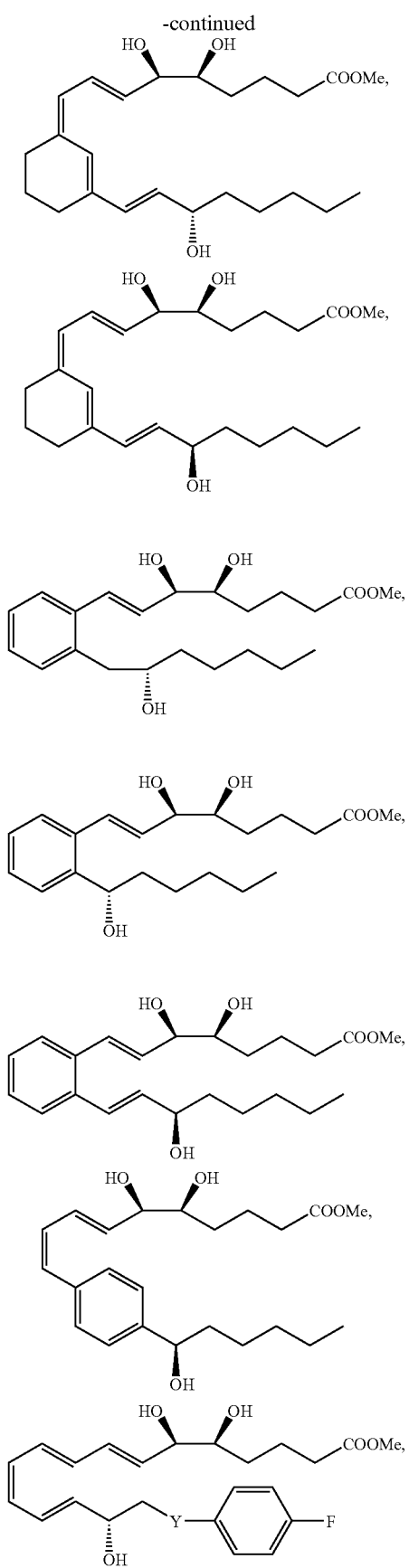
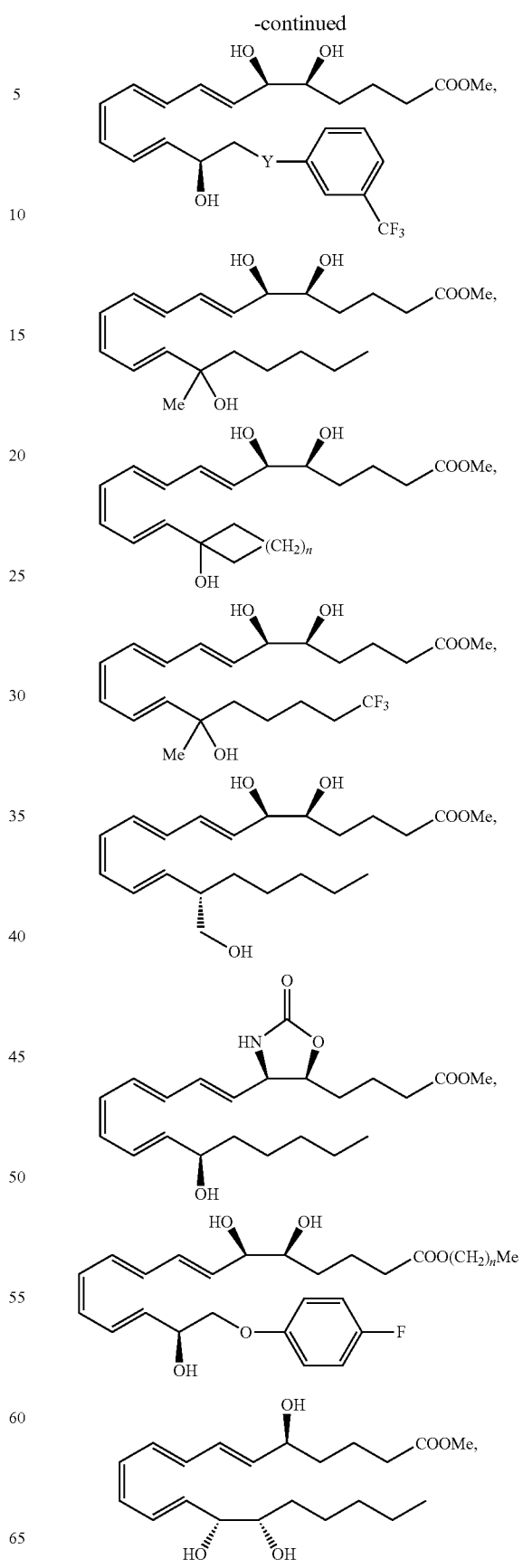

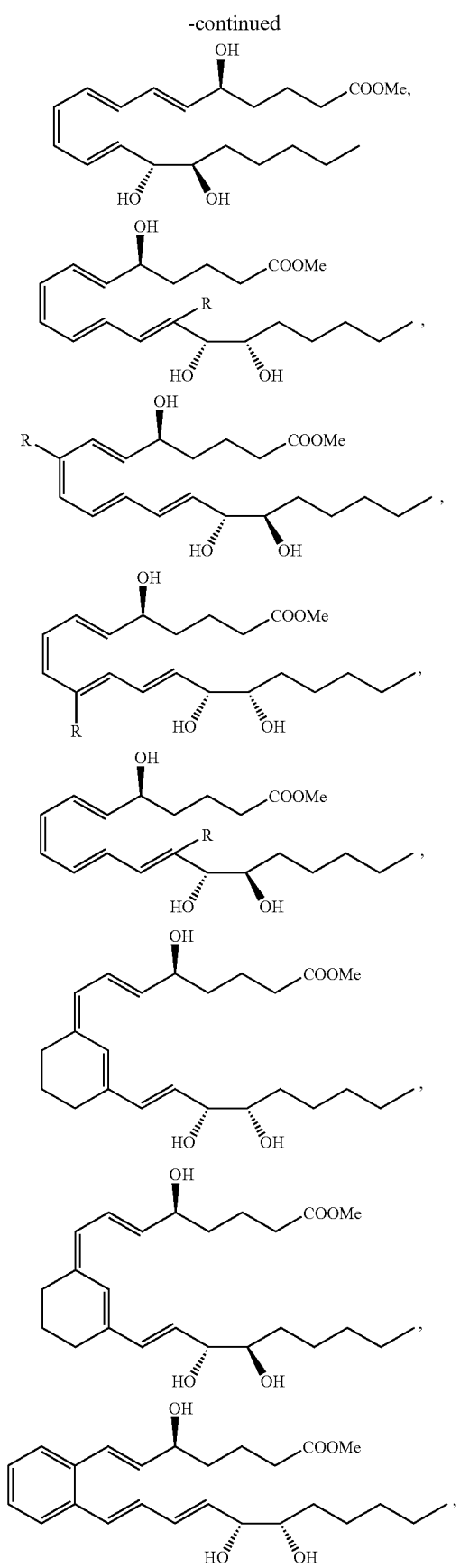
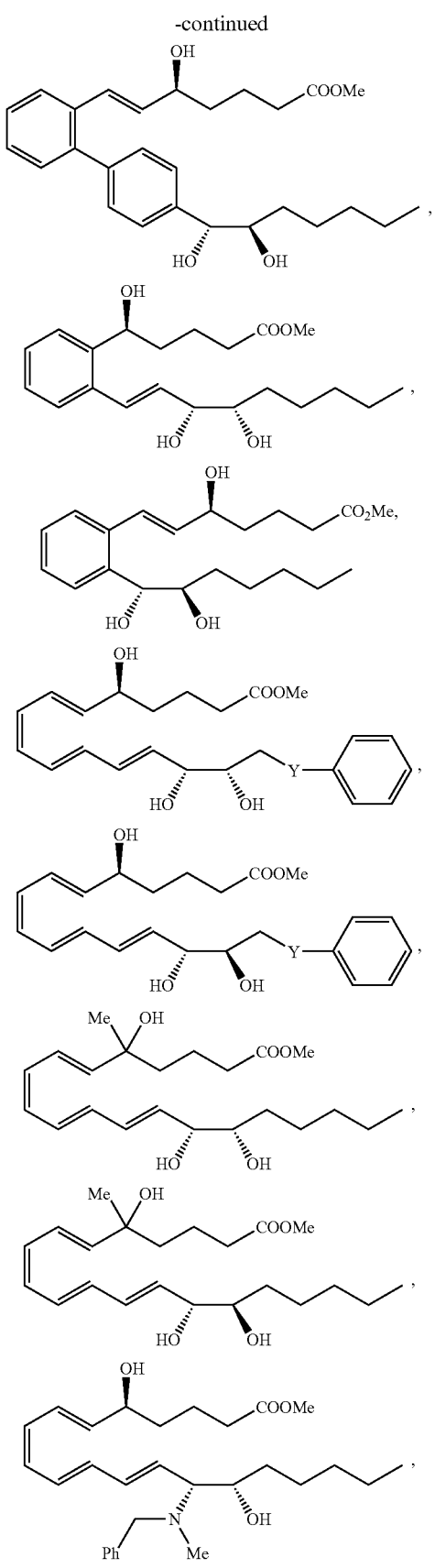

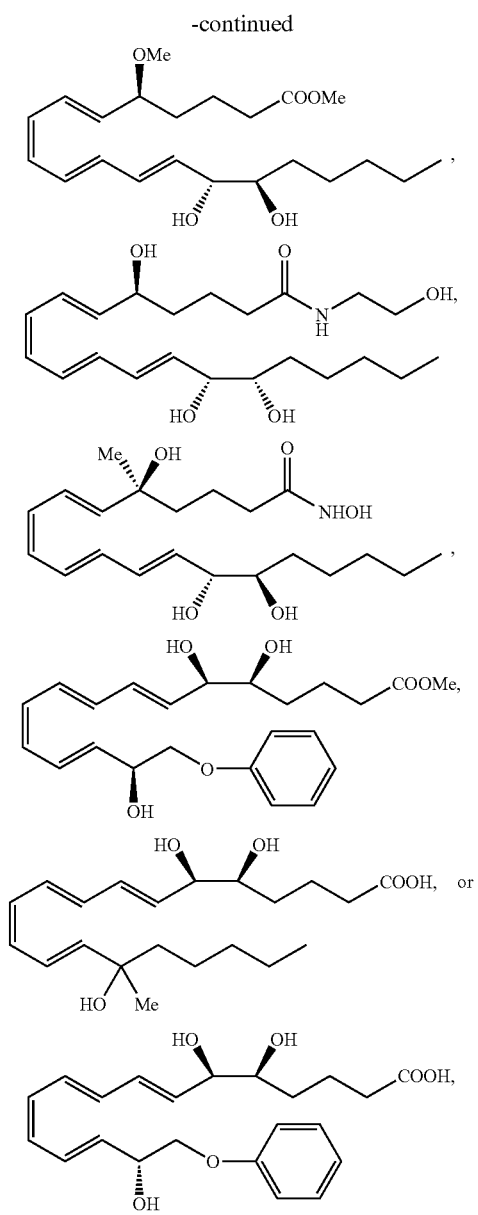

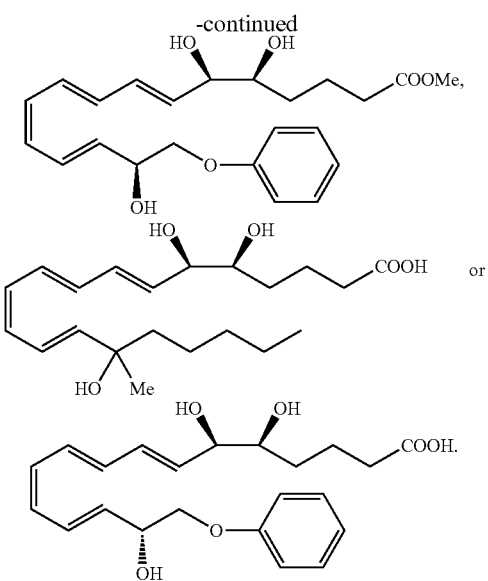

4. The method according to claim 1, wherein the compound corresponds to any one of the formulae:

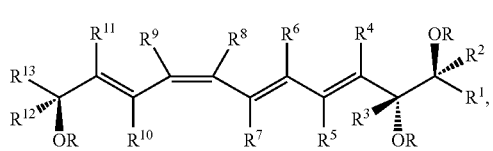
LXA$_4$/LXB$_4$ analog

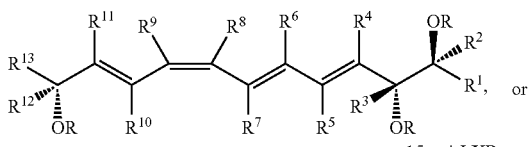
15-epi-LXA$_4$ analog

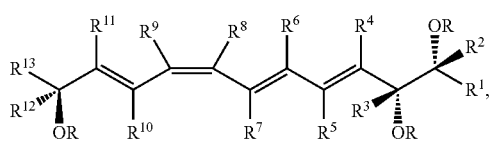
15-epi-LXB$_4$ analog wherein:
R is selected from the group consisting of:
(i) hydrogen; and
(ii) straight, branched, cyclic, saturated, or unsaturated alkyl having from 1 to 20 carbon atoms;
R$^1$, R$^2$, R$^{12}$, and R$^{13}$ are independently selected from the group consisting of:
(i) hydrogen;
(ii) straight, branched, cyclic, saturated, or unsaturated alkyl having from 1 to 20 carbon atoms;
(iii) substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl wherein R is selected from the group consisting of methyl and phenyl, Y is selected from the group consisting of oxygen and CH$_2$, and n is 1 to 10.

3. The method according to claim 2, wherein the compound is:

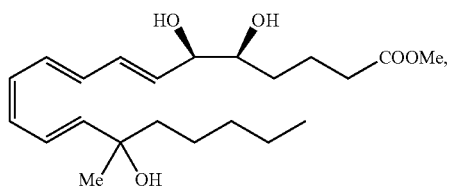

or heteroaryl, wherein the aryl or heteroaryl is substituted with one or more substituents selected from the group consisting of alkyl, cycloalkyl, alkoxy, halo, aryl, heteroaryl, carboxyl, and carboxamido; and (iv) a group Z-Y, wherein:

Z is selected from the group consisting of a straight, branched, cyclic, saturated, or unsaturated alkyl having from 1 to 20 carbon atoms; substituted lower alkyl, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; and substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and Y is selected from the group consisting of hydrogen; alkyl; cycloalkyl; carboxyl; carboxamido; aryl; heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido;

$R^3$ selected from the group consisting of:

(i) hydrogen;

(ii) straight, branched, cyclic, saturated, or unsaturated alkyl having from 1 to 20 carbon atoms;

(iii) substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and (iv) a group Z-Y, wherein:

Z is selected from the group consisting of a branched, cyclic, or unsaturated alkyl having from 1 to 20 carbon atoms; substituted lower alkyl, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; and substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and Y is selected from the group consisting of hydrogen; alkyl; cycloalkyl; carboxyl; carboxamido; aryl; heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido; and $R^4$, $R^5$, $R^6$, $R^7$, $R^8$, $R^9$, $R^{10}$ and $R^{11}$ are independently selected from a group consisting of:

(i) hydrogen;

(ii) halo;

(iii) straight, branched, cyclic, saturated, or unsaturated alkyl having from 1 to 20 carbon atoms; and (iv) substituted alkyl having from 1 to 20 carbon atoms, wherein the alkyl is substituted with one or more substituents selected from the group consisting of halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl, and heteroaryl; substituted aryl or heteroaryl, wherein the aryl or heteroaryl is substituted with one or more substituents selected from the group consisting of alkyl, cycloalkyl, alkoxy, halo, aryl, heteroaryl, carboxyl, and carboxamido;

wherein, optionally, one or more pairs selected from $R^1$, $R^2$, $R^3$, $R^4$, $R^5$, $R^6$, $R^7$, $R^8$, $R^9$, $R^{10}$, $R^{11}$, $R^{12}$ and $R^{13}$ are independently replaced with a bond that forms a carbon-carbon double bond, a carbon-carbon triple bond, or a ring with the lipoxin backbone optionally substituted with one or more halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl or heteroaryl groups, and wherein, optionally, one or more pairs selected from R, $R^1$, $R^2$, $R^3$, $R^4$, $R^5$, $R^6$, $R^7$, $R^8$, $R^9$, $R^{10}$, $R^{11}$, $R_{12}$ and $R^{13}$ are independently connected to form one or more rings containing 3 to 20 carbon atoms, wherein the rings optionally contain 1 to 6 oxygen atoms, 1 to 6 nitrogen atoms, or both 1 to 6 oxygen atoms and 1 to 6 nitrogen atoms, and wherein the rings are optionally substituted with one or more halo, hydroxy, lower alkoxy, aryloxy, amino, alkylamino, dialkylamino, acylamino, arylamino, hydroxyamino, alkoxyamino, alkylthio, arylthio, carboxy, carboxamido, carboalkoxy, aryl or heteroaryl groups.

5. The method according to claim 4, wherein the compound is of the formula:

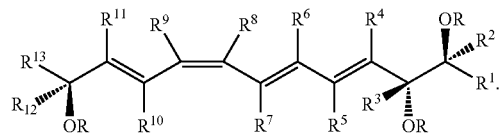

$LXA_4/LXB_4$ analog

6. The method according to claim 5, wherein the compound is:

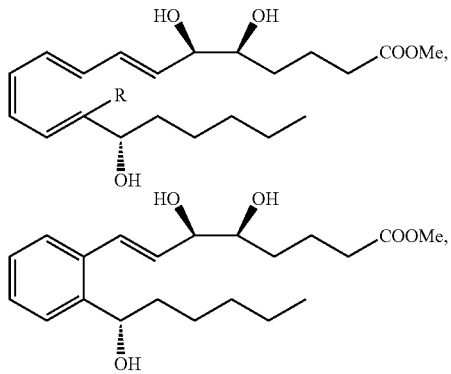

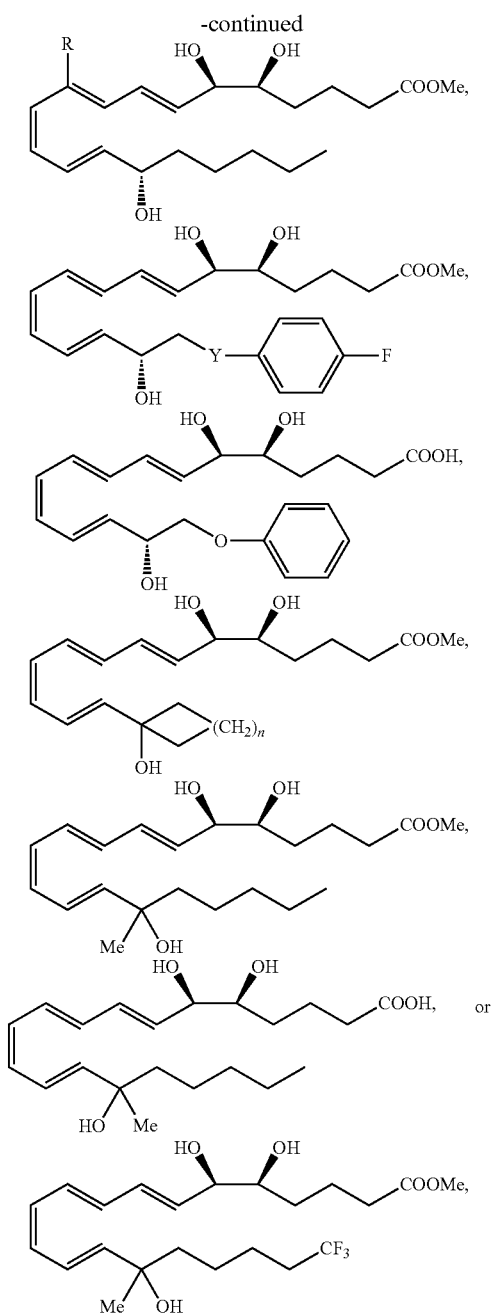
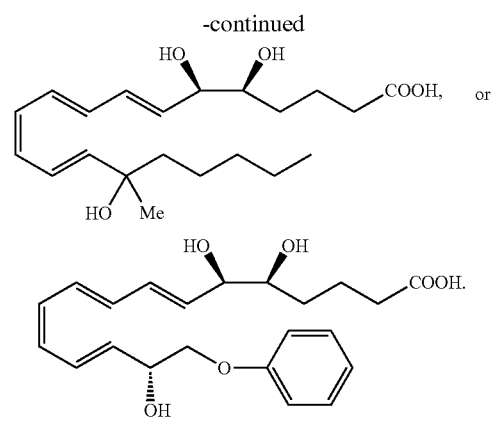
wherein R is selected from the group consisting of methyl and phenyl, Y is selected from the group consisting of oxygen and CH₂, and n is 1 to 10.
7. The method according to claim 6, wherein the compound is:
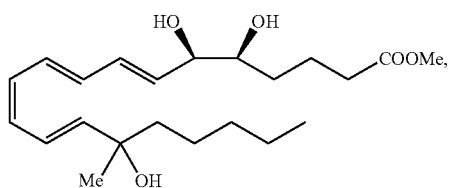
8. The method according to claim 5, wherein the compound is:
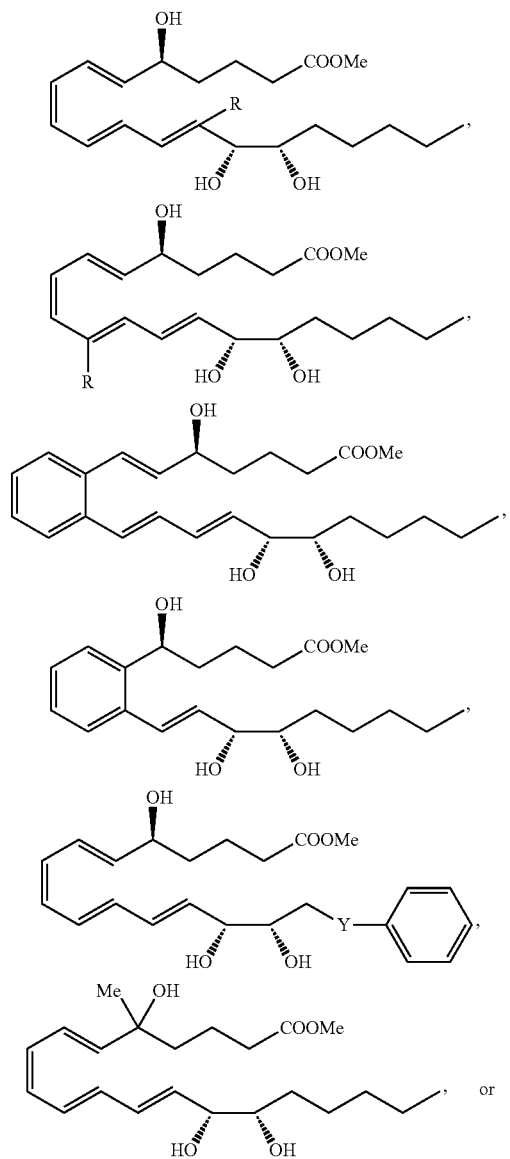

-continued

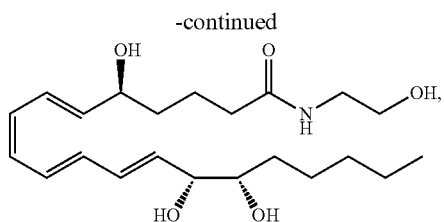

wherein R is selected from the group consisting of methyl and phenyl, and Y is selected from the group consisting of oxygen and $CH_2$, and n is 1 to 10.

9. The method according to claim 4, wherein the compound is of the formula

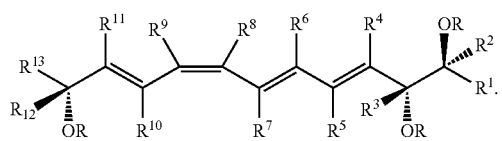

15-epi-LXA$_4$ analog

10. The method according to claim 9, wherein the compound is:

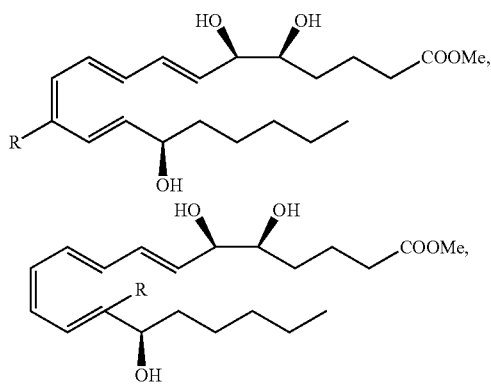

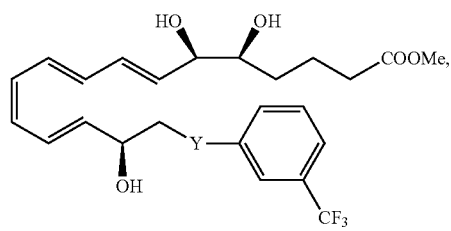

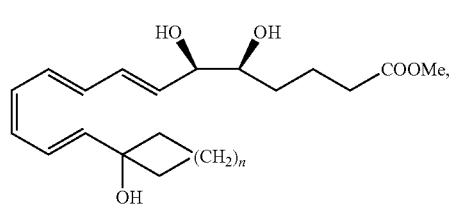

-continued

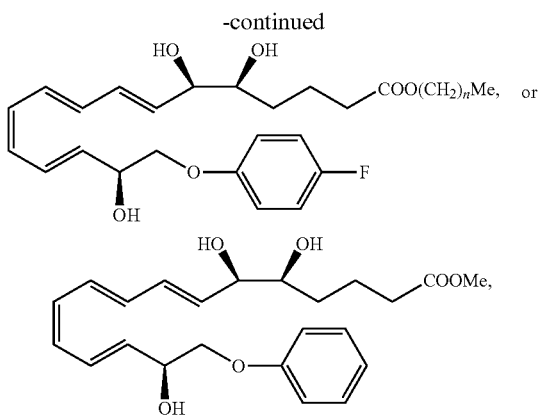

wherein R is selected from the group consisting of methyl and phenyl, and Y is selected from the group consisting of oxygen and $CH_2$, and n is 1 to 10.

11. The method according to claim 10, wherein the compound is:

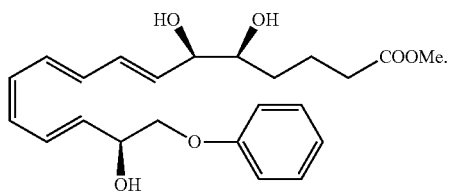

12. The method according to claim 4, wherein the compound is of the formula:

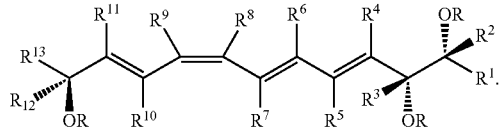

15-epi-LXB$_4$ analog

13. The method according to claim 12, wherein the compound is:

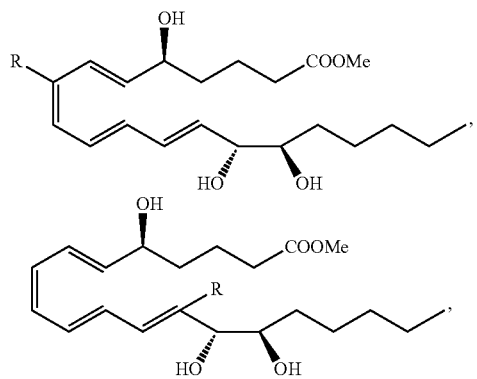

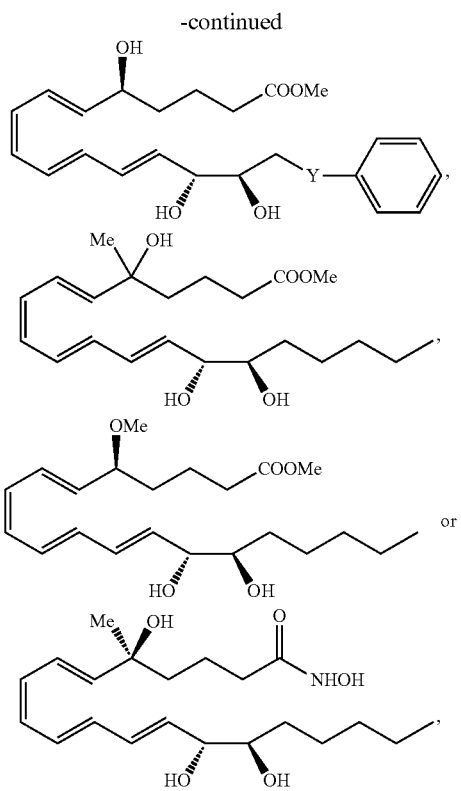

wherein R is selected from the group consisting of methyl and phenyl, and Y is selected from the group consisting of oxygen and CH₂.

14. The method according to claim 1, wherein the periodontal disease is gingivitis.

15. The method according to claim 1, wherein the periodontal disease is periodontitis.

16. The method according to claim 1, wherein the periodontal disease is aphthous ulcer.

17. The method according to claim 1, wherein the periodontal disease is herpetic stomatitis.

18. The method according to claim 1, wherein the administration is topical oral administration.

19. The method according to claim 1, wherein the composition further comprises a COX-2 inhibitor.

20. The method according to claim 19, wherein the COX-2 inhibitor is celecoxib, rofecoxib or valdecoxib.

21. The method according to claim 2, wherein the compound is:

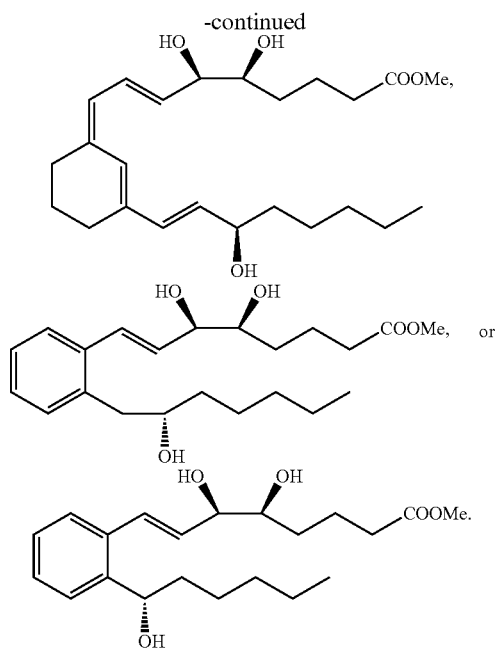

22. The method according to claim 2, wherein the compound is:

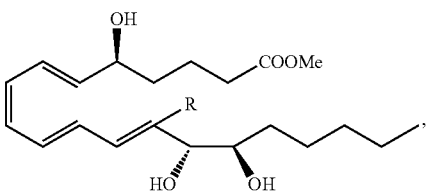

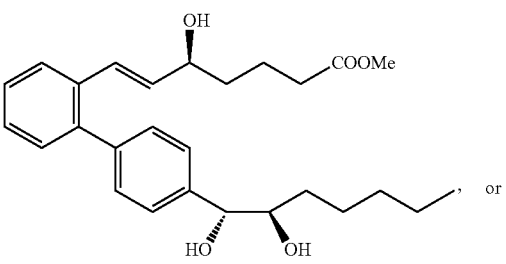

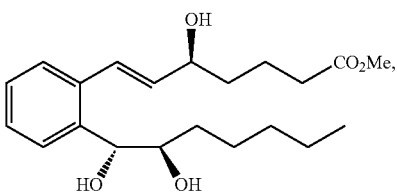

wherein R is selected from the group consisting of methyl and phenyl.

23. The method according to claim 2, wherein the compound is:

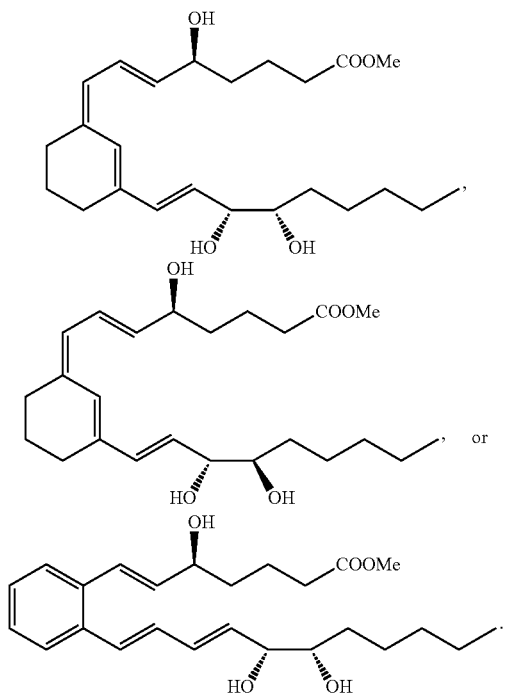

24. The method according to claim 6, wherein the compound is:

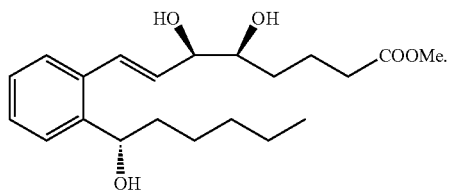

25. The method according to claim 8, wherein the compound is:

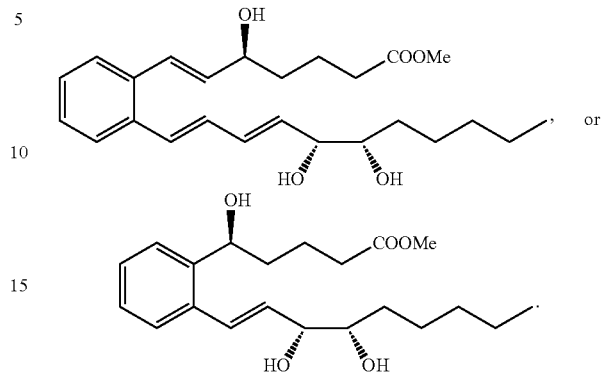

26. The method according to claim 13, wherein the compound is:

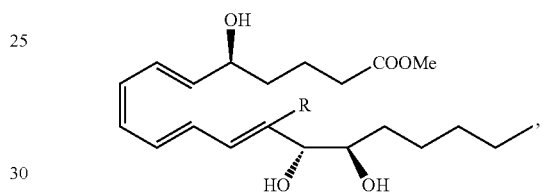

wherein R is selected from the group consisting of methyl and phenyl.

27. The method according to claim 1, wherein the compound is 15-R/S-methyl $LXA_4$.

28. The method according to claim 1, wherein the compound is 16-phenoxy $LXA_4$.

29. A method of preventing a periodontal disease in a human or animal comprising administering to the human or animal a prophylactically effective amount of a composition comprising a compound which is a structural analog of lipoxin $A_4$ ($LXA_4$), lipoxin $B_4$ ($LXB_4$), 15-epi-lipoxin $A_4$ (15-epi-$LXA_4$) or 15-epi-lipoxin $B_4$ (1 5-epi-$LXB_4$).

* * * * *

SEQUENCE LISTING

<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: synthetic primer for human COX-2

<400> SEQUENCE: 1
gctgactatg gctacaaaag ctgg                                          24

<210> SEQ ID NO 2
<211> LENGTH: 24
<212> TYPE: DNA
<213> ORGANISM: Artificial Sequence
<220> FEATURE:
<223> OTHER INFORMATION: synthetic primer for human COX-2

<400> SEQUENCE: 2
atgctcaggg acttgaggag ggta                                          24

<210> SEQ ID NO 3
<211> LENGTH: 21
<212> TYPE: DNA
<213> ORGANISM: Artificial Sequence
<220> FEATURE:
<223> OTHER INFORMATION: synthetic primer for murine COX-2

```
<400> SEQUENCE: 3
aactcccatg ggtgtgaagg g                                        21

<210> SEQ ID NO 4
<211> LENGTH: 21
<212> TYPE: DNA
<213> ORGANISM: Artificial Sequence
<220> FEATURE:
<223> OTHER INFORMATION: synthetic primer for murine COX-2

<400> SEQUENCE: 4
ccaaagatag catctggacg a                                        21

<210> SEQ ID NO 5
<211> LENGTH: 22
<212> TYPE: DNA
<213> ORGANISM: Porphyromonas gingivalis

<400> SEQUENCE: 5
ggcaggcgga attcgtggtg ta                                       22

<210> SEQ ID NO 6
<211> LENGTH: 24
<212> TYPE: DNA
<213> ORGANISM: Porphyromonas gingivalis

<400> SEQUENCE: 6
gatgtaaggg ccgtgctgat ttga                                     24
```